(12) United States Patent
Elmaanaoui et al.

(10) Patent No.: US 12,112,488 B2
(45) Date of Patent: Oct. 8, 2024

(54) METHODS AND SYSTEMS FOR IMAGE SYNCHRONIZATION

(71) Applicant: Canon U.S.A., Inc., Melville, NY (US)

(72) Inventors: Badr Elmaanaoui, Belmont, MA (US); James Hastings Houskeeper, Mendon, MA (US)

(73) Assignee: Canon U.S.A., Inc., Melville, NY (US)

( * ) Notice: Subject to any disclaimer, the term of this patent is extended or adjusted under 35 U.S.C. 154(b) by 202 days.

(21) Appl. No.: 17/381,048

(22) Filed: Jul. 20, 2021

(65) Prior Publication Data

US 2022/0044428 A1 Feb. 10, 2022

Related U.S. Application Data

(60) Provisional application No. 63/062,159, filed on Aug. 6, 2020.

(51) Int. Cl.
*G06T 7/30* (2017.01)
*A61B 5/00* (2006.01)
*A61B 34/20* (2016.01)

(52) U.S. Cl.
CPC .............. *G06T 7/30* (2017.01); *A61B 5/0066* (2013.01); *A61B 5/0071* (2013.01); *A61B 5/0075* (2013.01); *A61B 34/20* (2016.02); *G06T 2207/10064* (2013.01); *G06T 2207/10101* (2013.01); *G06T 2207/30004* (2013.01)

(58) Field of Classification Search
CPC ... A61B 5/0066; A61B 5/0071; A61B 5/0075; A61B 34/20; G06T 2207/10064; G06T 2207/10101; G06T 2207/30004; G06T 7/30

See application file for complete search history.

(56) References Cited

U.S. PATENT DOCUMENTS

| | | |
|---|---|---|
| 6,292,681 B1 | 9/2001 | Moore |
| 7,872,759 B2 | 1/2011 | Tearney et al. |
| 7,889,348 B2 | 2/2011 | Tearney et al. |

(Continued)

FOREIGN PATENT DOCUMENTS

| | | |
|---|---|---|
| CN | 104257342 A | 1/2015 |
| CN | 105188550 A | 12/2015 |

(Continued)

OTHER PUBLICATIONS

Benoit Godbout, et al., "3D Elastic Registration of Vessel Structures from IVUS Data on Biplane Angiography", Academic Radiology, vol. 12, No. 1, Jan. 2005, pp. 10-16.

*Primary Examiner* — Baisakhi Roy
(74) *Attorney, Agent, or Firm* — Canon U.S.A., Inc.

(57) ABSTRACT

One or more devices, systems, methods, and storage mediums for performing image synchronization using one or more imaging modalities are provided herein. Examples of applications include imaging, evaluating and diagnosing biological objects, such as, but not limited to, for Gastrointestinal, cardio and/or ophthalmic applications, and being obtained via one or more optical instruments, such as, but not limited to, optical probes, catheters, capsules and needles (e.g., a biopsy needle). Devices, systems, methods, and storage mediums may include or involve a method, such as, but not limited to, for performing image synchronization.

22 Claims, 14 Drawing Sheets

(56) References Cited

U.S. PATENT DOCUMENTS

| | | | |
|---|---|---|---|
| 7,918,793 B2* | 4/2011 | Altmann | A61B 5/283 600/466 |
| 8,145,293 B2 | 3/2012 | Zhang et al. | |
| 8,289,522 B2 | 10/2012 | Tearney et al. | |
| 8,928,889 B2 | 1/2015 | Tearney et al. | |
| 9,087,368 B2* | 7/2015 | Tearney | A61B 5/0062 |
| 9,332,942 B2 | 5/2016 | Jaffer et al. | |
| 9,646,377 B2* | 5/2017 | Tearney | A61B 5/7271 |
| 9,763,623 B2 | 9/2017 | Tearney et al. | |
| 9,907,527 B2 | 3/2018 | Dascal et al. | |
| 10,987,000 B2* | 4/2021 | Tearney | G06T 7/0012 |
| 11,123,047 B2* | 9/2021 | Jaffer | A61B 8/5261 |
| 2006/0195014 A1 | 8/2006 | Seibel et al. | |
| 2007/0055155 A1* | 3/2007 | Owen | A61B 8/00 600/439 |
| 2007/0081236 A1 | 4/2007 | Tearney | G01B 9/02064 359/390 |
| 2007/0232892 A1 | 10/2007 | Hirota | |
| 2009/0143686 A1* | 6/2009 | Onimura | A61B 5/0073 356/477 |
| 2009/0156937 A1* | 6/2009 | Sasaki | A61B 8/483 600/447 |
| 2009/0234231 A1 | 9/2009 | Knight et al. | |
| 2009/0318807 A1* | 12/2009 | Katoh | A61B 5/02007 600/443 |
| 2010/0092389 A1 | 4/2010 | Jaffer | |
| 2011/0071405 A1 | 3/2011 | Judell et al. | |
| 2012/0101374 A1 | 4/2012 | Tearney et al. | |
| 2013/0216114 A1 | 8/2013 | Courtney et al. | |
| 2014/0187963 A1 | 7/2014 | Corl | |
| 2014/0188503 A1 | 7/2014 | Balignasay et al. | |
| 2015/0202408 A1* | 7/2015 | McMurtry | A61M 25/01 604/95.01 |
| 2016/0228097 A1 | 8/2016 | Jaffer et al. | |
| 2017/0245822 A1* | 8/2017 | Vaillant | A61B 5/7289 |
| 2018/0003481 A1 | 1/2018 | Yamada et al. | |
| 2018/0045501 A1 | 2/2018 | Elmaanaoui | |
| 2018/0368698 A1* | 12/2018 | Oyama | A61B 8/4494 |
| 2019/0059734 A1* | 2/2019 | Yamada | A61B 5/0066 |
| 2019/0083062 A1 | 3/2019 | Barone et al. | |
| 2019/0105015 A1 | 4/2019 | Stigall et al. | |
| 2019/0132570 A1* | 5/2019 | Chen | H04N 23/60 |
| 2019/0219496 A1 | 7/2019 | Sakamoto et al. | |
| 2019/0321005 A1* | 10/2019 | Sasaki | A61B 8/42 |
| 2019/0374109 A1 | 12/2019 | Wu et al. | |
| 2020/0046283 A1 | 2/2020 | Tearney et al. | |
| 2021/0077037 A1 | 3/2021 | Kunio | |
| 2021/0169336 A1* | 6/2021 | Sanchez | A61B 5/444 |
| 2021/0174125 A1 | 6/2021 | Zhang | |
| 2022/0007943 A1* | 1/2022 | Sanchez | A61B 5/0075 |
| 2022/0044428 A1* | 2/2022 | Elmaanaoui | A61B 5/6852 |

FOREIGN PATENT DOCUMENTS

| | | |
|---|---|---|
| CN | 109219415 A | 1/2019 |
| JP | 2001232853 A | 8/2001 |
| JP | 2011-072596 A | 4/2011 |
| JP | 2013-541392 A | 11/2013 |
| JP | 2018-169246 A | 11/2018 |
| JP | WO2018/061672 A1 | 7/2019 |
| WO | 2016/140116 A1 | 9/2016 |

* cited by examiner

METHODS AND SYSTEMS FOR IMAGE SYNCHRONIZATION

CROSS-REFERENCE TO RELATED APPLICATION(S)

This application relates, and claims priority, to U.S. patent application Ser. No. 63/062,159, filed Aug. 6, 2020, the entire disclosure of which is incorporated by reference herein in its entirety.

FIELD OF THE DISCLOSURE

The present disclosure relates generally to the field of imaging and more particularly to one or more optical apparatuses, systems, methods (for using and/or manufacturing) and storage mediums, such as, but not limited to, fiber optic catheters, endoscopes and/or optical coherence tomography (OCT) and/or fluorescence apparatuses and systems, and methods and storage mediums, for use with same, for image synchronization when obtaining image(s), such as with pullback mechanisms, for one or more imaging modalities, such as OCT or other (e.g., intravascular ultrasound (IVUS), other imaging modalities for image(s) or lumen image(s), etc.). Examples of such applications include imaging, evaluating and diagnosing biological objects, such as, but not limited to, gastro-intestinal, pulmonary, cardio, ophthalmic, and/or intravascular applications, and being obtained via one or more optical instruments, such as, but not limited to, one or more optical probes, one or more catheters, one or more endoscopes, one or more phase shift units (e.g., galvanometer scanner), one or more tethered capsules, one or more needles (e.g., a biopsy needle), and one or more bench top systems.

BACKGROUND

Fiber optic catheters and endoscopes have been developed to access to internal organs. For example in cardiology, OCT has been developed to see depth resolved images of vessels with a catheter. The catheter, which may include a sheath, a coil and an optical probe, may be navigated to a coronary artery.

Optical coherence tomography (OCT) is a technique for obtaining high-resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are. Single mode fibers may be used for OCT optical probes, and double clad fibers may be used for fluorescence and/or spectroscopy.

Percutaneous coronary intervention (PCI), and other vascular diagnosis and intervention procedures, have improved with the introduction of intravascular imaging (IVI) modalities, such as, but not limited to, intravascular ultrasound (IVUS) and optical coherence tomography (OCT). IVI modalities provide cross-sectional imaging of coronary arteries with precise lesion information (e.g., lumen size, plaque morphology, implanted devices, etc.). That said, only about 20% of interventional cardiologists in the United States use IVI imaging in conjunction with coronary angiography during PCI procedures.

Prior systems tried to rely on: (i) estimating a delay between an issue of a pullback start command and an actual start of a pullback mechanism and accounting for the delay in order to time a first acquisition frame; (ii) using image processing techniques to estimate which acquisition frame corresponds to start of a pullback; or (iii) using two signals from a scanning mechanism to inform the acquisition of the start of the pullback and of rotation information.

However, such prior systems do not perform image synchronization based on pullback mechanisms, including automatic pullback mechanisms. In such prior systems, data may not be properly aligned with a scanning mechanism, and may lead to undesirable outcomes, such as, but not limited to, erroneous measurement of object feature(s), ending of imaging recording too prematurely, recording more data than is necessary, etc.

Accordingly, there is a need for synchronization of images with pullback mechanisms and/or automatic pullback mechanisms, especially in cases where a start of a pullback may be either manually or algorithmically trigged. It also would be desirable to provide one or more image synchronization techniques and/or structure for use in at least one optical device, assembly or system to achieve consistent, reliable image synchronization results at high efficiency and a reasonable cost of manufacture and maintenance.

SUMMARY OF THE DISCLOSURE

Accordingly, it is a broad object of the present disclosure to provide imaging (e.g., OCT, NIRAF, etc.) apparatuses, systems, methods and storage mediums for using and/or controlling one or more imaging modalities and/or to perform synchronization of image(s) with pullback mechanism(s) with one or more imaging apparatuses, systems, storage mediums, etc. It is also a broad object of the present disclosure to provide OCT devices, systems, methods and storage mediums using an interference optical system, such as an interferometer (e.g., spectral-domain OCT (SD-OCT), swept-source OCT (SS-OCT), multimodal OCT (MM-OCT), Intravascular Ultrasound (IVUS), Near-Infrared Autofluorescence (NIRAF), Near-Infrared Spectroscopy (NIRS), Near-Infrared Fluorescence (NIRF), therapy modality using light, sound, or other source of radiation, etc.).

One or more embodiments of the present disclosure relate generally to at least the field of imaging that uses synchronization of images with pullback mechanisms. Examples of such applications include, but are not limited to, imaging, evaluation and diagnosis of biological objects, such as, but not limited to, gastro-intestinal, pulmonary and/or intravascular applications, being obtained via one or more instruments, such as, but not limited to, one or more probes, one or more catheters, one or more endoscopes, one or more tethered capsules, and one or more needles (e.g., a biopsy needle).

In one or more embodiments, intraluminal imaging aims to acquire high-resolution cross-sectional images of tissue and enable real time visualization. Intraluminal imaging may use manually triggered, algorithmically triggered, and/or automatically triggered scanning of an optical probe with simultaneous system recording of the data. In one or more embodiments, the data may be aligned with an actual physical motion of the probe, which may be performed using what is referred to herein as a scanning mechanism preferably for one or more apparatuses or systems to function as desired.

At least one embodiment of an imaging system in accordance with the present disclosure was prototyped to investigate the feasibility of synchronizing acquisition of images with probe location for the entire probe scanning. The probe in this case may be a catheter with fixed outer sheet and a rotatable and translatable inner core containing an optical fiber and distal optics to focus light on the sample.

One or more embodiments of the present disclosure provide one or more of the following advantages: reduces a number of PIU cable wires to achieve a more flexible PIU and/or PIU cable; reduces a number of auxiliary input for an HS digitizer making for a simpler design (and may be used with standard or off the shelf digitizer(s)); achieves image acquisition that may be synchronized with a pullback mechanism with use of any operating system without relying on a real time operating system or a global synchronization (or, in one or more embodiments, may be used with a real time operating system or a global synchronization); and/or provides a flexible design that may be used for distributed systems where a distance between data acquisition and a pullback mechanism is significant; etc.

One or more embodiments of the present disclosure may include an imaging apparatus or system, a scanning mechanism, and a single data acquisition synchronization signal or apparatus. Indeed, one or more embodiments of a system for image acquisition synchronization with imaging beam position may include: an imaging system, a scanning mechanism, and a single data acquisition synchronization signal or apparatus.

In one or more embodiments, a system for performing image synchronization may include: an imaging apparatus or system using one or more imaging modalities to obtain imaging data; a scanning mechanism that operates to perform beam scanning of a catheter or probe of the system to obtain a beam position of the catheter or probe; and one or more processors that operate to achieve image synchronization by recording the beam position simultaneously or contemporaneously with the imaging data and that operate to enable accurate spatial registration of the imaging data.

In one or more embodiments, the one or more processors may further include a data acquisition processor and a hardware management processor, the hardware management processor operating to control the data acquisition processor and the data acquisition processor operating to acquire the imaging data obtained by the imaging apparatus or system.

In one or more embodiments, the system may further include: (i) a rotary motor that operates to rotate the scanning mechanism, a part of the scanning mechanism, and/or the catheter or probe, and (ii) a pullback motor that operates to control pullback of the catheter or probe, wherein the catheter or probe beam scanning is performed by the scanning mechanism using the rotary motor and the pullback motor.

In one or more embodiments, one or more of the following may occur: (i) the one or more processors further include a data acquisition processor and a hardware management processor, the hardware management processor operating to control the data acquisition processor and the data acquisition processor operating to acquire the imaging data obtained by the imaging apparatus or system; (ii) the system further includes a rotary motor controller and a pullback motor controller, the rotary motor controller operating to control the rotary motor, and the pullback motor controller operating to control the pullback motor; (iii) the system further includes a rotary motor controller and a pullback motor controller, the rotary motor controller operating to control the rotary motor, and the pullback motor controller operating to control the pullback motor, and the one or more processors include a control processor that operates to control, or send commands to, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns; (iv) the one or more processors include a synchronization processor, and the system further includes a first encoder signal that operates to be available to the rotary motor controller and a second encoder signal that operates to be available to the pullback motor controller, wherein the synchronization processor operates to condition or control the first and second encoder signals; and/or (v) the one or more processors include a synchronization processor, and the system further includes a first encoder signal that operates to be available to the rotary motor controller and a second encoder signal that operates to be available to the pullback motor controller, wherein the synchronization processor operates to condition or control the first and second encoder signals before the synchronization processor interfaces with the data acquisition processor such that each time a depth scan is acquired on the imaging data input, information from the encoder signals is recorded for each of the rotary motor and the pullback motor to record an exact or approximate beam position for the depth scan.

In one or more embodiments, the one or more processors further include a data acquisition processor operating to acquire the imaging data obtained by the imaging apparatus or system; and the one or more processors include a synchronization processor, and the system further includes a first encoder signal that operates to be available to the rotary motor controller and a second encoder signal that operates to be available to the pullback motor controller, wherein the synchronization processor operates to condition or control the first and second encoder signals before the synchronization processor interfaces with the data acquisition processor such that each time a depth scan is acquired on the imaging data input, information from the encoder signals is recorded for each of the rotary motor and the pullback motor to record an exact or approximate beam position for the depth scan, and the synchronization processor operates to use a single synchronization signal for the data acquisition processor to capture a position of the catheter or probe for each measured depth scan profile, wherein one or more of the following: (i) a trigger signal is used to trigger a single acquisition of a depth scan and to record a value of a rotation digital counter and a pullback digital counter derived from a demodulated encoded synchronization signal that is demodulated with a demodulator of the system and/or of the data acquisition processor of the system; (ii) a trigger signal is used to trigger a single acquisition of a depth scan on an analog-to-digital converter (ADC) and to record a rotation digital counter and a pullback digital counter derived from a demodulated encoded synchronization signal that is demodulated with a demodulator of the system and/or of the data acquisition processor of the system; (iii) the trigger signal is an A-line trigger signal that operates to trigger a sampling of the imaging data, or the trigger signal is a k-clock trigger signal that operates to trigger a sampling of the imaging data so as to uniformly acquiring the imaging data in k space; (iv) the synchronization signal includes or comprises resultant pulse trains which are a result or are resultant of superimposition of pulse trains from each of the first and second encoder signals that operate to switch at a defined rate per revolution of the rotary motor and/or the pullback motor, and a rotation digital counter and a pullback digital counter of the data acquisition processor operate to count the switches such that current positions of the rotary motor and the pullback motor are measured; (v) the encoder signal pulses have a 2 volt (V) amplitude for the rotary motor encoder signal and a 3V amplitude for the pullback motor encoder signal, the rotational digital counter operates to be incremented at one or more of the following transitions: at a transition from 0V to 2V, at a transition from 3V to 5V, and/or at a transition from 0V to 5V, and the pullback digital counter operates to be incremented at one or more of the following transitions: at a transition from 0V to 3V, at a transition from 2V to 5V, and/or at a transition from 0V to 5V; and/or (vi) the ADC, the demodulator, and the rotation digital counter and the pullback digital counter are included in the data acquisition processor.

In one or more embodiments, the one or more processors further include a data acquisition processor operating to acquire the imaging data obtained by the imaging apparatus or system; and the one or more processors include a synchronization processor, and the system further includes a first encoder signal that operates to be available to the rotary motor controller and a second encoder signal that operates to be available to the pullback motor controller, wherein the synchronization processor operates to condition or control the first and second encoder signals before the synchronization processor interfaces with the data acquisition processor such that each time a depth scan is acquired on the imaging data input, information from the encoder signals is recorded for each of the rotary motor and the pullback motor to record an exact or approximate beam position for the depth scan, and the synchronization processor operates to use a single synchronization signal for the data acquisition processor to capture a position of the catheter or probe for each measured depth scan profile, wherein one or more of the following: (i) a trigger signal is used to trigger a single acquisition of a depth scan and to record a value of a rotation digital counter and a pullback digital counter derived from a demodulated encoded synchronization signal that is demodulated with a demodulator of the system and/or of the data acquisition processor of the system; (ii) a trigger signal is used to trigger a single acquisition of a depth scan on an analog-to-digital converter (ADC) and to record a rotation digital counter and a pullback digital counter derived from a demodulated encoded synchronization signal that is demodulated with a demodulator of the system and/or of the data acquisition processor of the system; (iii) the trigger signal is an A-line trigger signal that operates to trigger a sampling of the imaging data, or the trigger signal is a k-clock trigger signal that operates to trigger a sampling of the imaging data so as to uniformly acquiring the imaging data in k space; and/or (iv) the synchronization signal includes or comprises resultant pulse trains which are pulse trains coming from the synchronization processor, and the synchronization processor operates to send a pulse corresponding to an index of the first encoder signal which occurs per rotation of the rotary motor except the synchronization processor modifies the pulse at a predetermined or set portion of the pullback, the predetermined or set portion of the pullback being one or more of the following: a start of the pullback where the synchronization processor modifies the pulses in such a way that the synchronization processor blanks or skips one pulse at the start of the pullback, an end of the pullback where the synchronization processor modifies the pulses in such a way that the synchronization processor blanks or skips one pulse at an end of the pullback, a start and an end of the pullback where the synchronization processor modifies the pulses in such a way that the synchronization processor blanks or skips one pulse at the start of the pullback and then another pulse at the end of the pullback, a start and/or an end of the pullback where the synchronization processor modifies the pulse in such a way that the synchronization processor introduces extra pulses and/or delays at the start of the pullback and/or at the end of the pullback, at an end of the pullback where the synchronization processor modifies the pulse to increment a frame counter of the data acquisition processor at a slower rate as the rotary motor is decelerating, and/or at a start of the pullback where the synchronization processor modifies the pulse to increment a frame counter of the data acquisition processor towards a steady rate as the rotary motor accelerates to a steady state target.

In one or more embodiments, one or more of the following may occur: (i) the data acquisition processor includes a frame counter that is incremented at a fixed, stable, or predetermined or set rate, except at a start of a pullback where the frame counter increments at about half of the predetermined or set rate or at a portion of the predetermined or set rate such that a jump between the start of the pullback and a time when the frame counter is incremented at the fixed, stable, or predetermined or set rate signals or indicates the start and/or the end of the pullback accurately and deduces an approximate or accurate recording of an exact beam position for each depth scan in a case where total pullback length and/or time is known or set; (ii) the one or more processors include a control processor that operates to control, or send commands to, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns, and the data acquisition processor includes a frame counter that is incremented at a fixed, stable, or predetermined or set rate, except, in a case where at an end of the pullback where the synchronization processor modifies the pulse to increment at a slower rate as the rotary motor is decelerating, the first encoder signal pulse trains are delayed further and the frame counter is incremented at an ever increasing number of A-line triggers, the rotary motor deceleration being controlled by the control processor or the one or more processors to coincide with the end of the pullback accurately to reduce or remove uncertainty between the end of the pullback and the start of the rotary motor deceleration and to determine the end of the pullback accurately and deduce the approximate or accurate recording of the exact beam position for each depth scan for a predetermined or set total pullback length and/or time; (iii) the rotary motor has a sharp deceleration profile and the rotary motor operates to decelerate significantly or substantially in one rotation for the number of A-line triggers occurring before the frame counter is incremented such that the deceleration profile of the rotary motor is large enough to be detected as the rotary motor slowing down rather than be detected as a variation in rotary motor rotation speed; and/or (iv) a variation in rotary motor speed operates to lead in normal operation to a pulse train every predetermined or set number of A-line triggers and the rotary motor deceleration during the time equivalent of one steady state rotation operates to be a number of A-line triggers that is larger than the predetermined or set number of A-line triggers such that a threshold value operates to be set or selected above A-line triggers and a threshold value operates to be set or selected below A-line triggers to detect the end of the pullback.

One or more embodiments may include or have one or more of the following: (i) the one or more processors further includes a pullback status processor that operates to determine a pullback status indicating or detecting the start and/or the end of the pullback; (ii) the deceleration of the rotary motor is initiated by the rotary motor controller and/or by the rotary motor controller and a driver, and the rotary motor controller and/or the driver operate to receive a command to control deceleration from the pullback status processor; (iii) the pullback status processor further operates to receive information from the rotary motor controller and/or the driver to determine the pullback status; and/or (iv) the pullback status processor is disposed or is included in the scanning mechanism of the system.

In one or more embodiments, one or more of the following may occur or exist: (i) the rotary motor is rotated at a velocity that is lower than a target steady state value, and then accelerated at or about the same time as the pullback motor is accelerated; (ii) the data acquisition processor includes a frame counter that is incremented at a fixed, stable, or predetermined or set rate once or as the rotary motor accelerates to the target steady state value; (iii) the one or more processors include a control processor that operates to control, or send commands to, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns, and the rotary motor acceleration is controlled by the control processor or the one or more processors to coincide with the start of the pullback accurately to reduce or remove uncertainty between the start of the pullback and the start of the rotary motor acceleration and to determine the start of the pullback accurately and deduce the approximate or accurate recording of the exact beam position for each depth scan for a predetermined or set total pullback length and/or time; (iv) the rotary motor has a sharp acceleration profile and the rotary motor operates to accelerate significantly or substantially in one rotation for the number of A-line triggers occurring before the frame counter is incremented such that the acceleration profile of the rotary motor is large enough to be detected as the rotary motor speeding up to the target steady state value rather than be detected as a variation in rotary motor rotation speed; and/or (v) a variation in rotary motor speed pre-pullback operates to lead to a pulse train every predetermined or set number of A-line triggers and the rotary motor acceleration during the time equivalent of one steady state rotation operates to be a number of A-line triggers that is larger than the predetermined or set number of A-line triggers such that a threshold value operates to be set or selected to detect the start of the pullback.

One or more embodiments may include or have one or more of the following: (i) the one or more processors further includes a pullback status processor that operates to determine a pullback status indicating or detecting the start and/or the end of the pullback; (ii) the acceleration of the rotary motor is initiated by the rotary motor controller and/or by the rotary motor controller and a driver, and the rotary motor controller and/or the driver operate to receive a command for controlling the acceleration from the pullback status processor; (iii) the pullback status processor further operates to receive information from the rotary motor controller and/or the driver to determine the pullback status; and/or (iv) the pullback status processor is disposed or is included in the scanning mechanism of the system.

In one or more embodiments, the system may further comprise or be connected to one or more of the following: a light source that operates to produce a light; an interference optical system that operates to: (i) receive and divide the light from the light source into a first light with which an object or sample is to be irradiated and a second reference light, (ii) send the second reference light for reflection off of a reference mirror of the interference optical system, and (iii) generate interference light by causing reflected or scattered light of the first light with which the object or sample has been irradiated and the reflected second reference light to combine or recombine, and to interfere, with each other, the interference light generating one or more interference patterns; and/or one or more detectors that operate to continuously acquire the interference light and/or the one or more interference patterns such that one or more A-lines or are obtained.

One or more embodiments may use one or more imaging modalities, wherein the one or more imaging modalities includes one or more of the following: Optical Coherence Tomography (OCT), single modality OCT, multi-modality OCT, swept source OCT, optical frequency domain imaging (OFDI), intravascular ultrasound (IVUS), another lumen image(s) modality, near-infrared spectroscopy, near-infrared fluorescence (NIRF), near-infrared auto-fluorescence (NIRAF), and an intravascular imaging modality.

In one or more embodiments, a method for controlling a system for performing image synchronization may include: using one or more imaging modalities to obtain imaging data using an imaging apparatus or system of the system; performing beam scanning, via a scanning mechanism of the system, of a catheter or probe of the system to obtain a beam position of the catheter or probe; and achieving image synchronization, via one or more processors of the system, by recording the beam position simultaneously or contemporaneously with the imaging data and enabling accurate spatial registration of the imaging data.

In one or more embodiments, the method may further include: controlling, via a hardware management processor, a data acquisition processor of the one or more processors, and acquiring, via the data acquisition processor, the imaging data obtained by the imaging apparatus or system.

One or more methods may include: (i) rotating the scanning mechanism, a part of the scanning mechanism, and/or the catheter or probe using a rotary motor, and (ii) controlling a pullback of the catheter or probe using a pullback motor, wherein the catheter or probe beam scanning is performed by the scanning mechanism using the rotary motor and the pullback motor.

One or more methods may include one or more of the following: (i) controlling, via a hardware management processor, a data acquisition processor of the one or more processors; (ii) acquiring, via the data acquisition processor, the imaging data obtained by the imaging apparatus or system; (iii) controlling the rotary motor using a rotary motor controller of the system and controlling the pullback motor using a pullback motor controller of the system; (iv) controlling, or sending commands to, via a control processor of the system, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns; (v) conditioning or controlling, via a synchronization processor of the one or more processors, first and second encoder signals, wherein the system further includes the first encoder signal that operates to be available to the rotary motor controller and the second encoder signal that operates to be available to the pullback motor controller; and/or (vi) conditioning or controlling, via a synchronization processor of the one or more processors, first and second encoder signals before the synchronization processor interfaces with the data acquisition processor such that each time a depth scan is acquired on the imaging data input, information from the first and second encoder signals is recorded for each of the rotary motor and the pullback motor to record an exact or approximate beam position for the depth scan, wherein the system further includes the first encoder signal that operates to be available to the rotary motor controller and the second encoder signal that operates to be available to the pullback motor controller.

In one or more method embodiments, the one or more processors further include a data acquisition processor operating to acquire the imaging data obtained by the imaging apparatus or system; and the one or more processors include a synchronization processor, and the system further includes a first encoder signal that operates to be available to the rotary motor controller and a second encoder signal that operates to be available to the pullback motor controller, wherein the synchronization processor operates to condition or control the first and second encoder signals before the synchronization processor interfaces with the data acquisition processor such that each time a depth scan is acquired on the imaging data input, information from the encoder signals is recorded for each of the rotary motor and the pullback motor to record an exact or approximate beam position for the depth scan, and the synchronization processor operates to use a single synchronization signal for the data acquisition processor to capture a position of the catheter or probe for each measured depth scan profile, wherein the method may include one or more of the following: (i) triggering, via a trigger signal of the system, a single acquisition of a depth scan and recording a value of a rotation digital counter and a pullback digital counter derived from a demodulated encoded synchronization signal that is demodulated with a demodulator of the system and/or of the data acquisition processor of the system; (ii) triggering, via a trigger signal of the system, a single acquisition of a depth scan on an analog-to-digital converter (ADC) and recording a rotation digital counter and a pullback digital counter derived from a demodulated encoded synchronization signal that is demodulated with a demodulator of the system and/or of the data acquisition processor of the system; (iii) triggering, via the trigger signal being an A-line trigger signal, a sampling of the imaging data, or triggering, via the trigger signal being a k-clock trigger signal, a sampling of the imaging data so as to uniformly acquiring the imaging data in k space; (iv) using the synchronization signal that includes or comprises resultant pulse trains which are a result or are resultant of superimposition of pulse trains from each of the first and second encoder signals that operate to switch at a defined rate per revolution of the rotary motor and/or the pullback motor, and counting, via a rotation digital counter and a pullback digital counter of the data acquisition processor, the switches such that current positions of the rotary motor and the pullback motor are measured; (v) using the encoder signal pulses have a 2 volt (V) amplitude for the rotary motor encoder signal and a 3V amplitude for the pullback motor encoder signal, wherein the rotational digital counter operates to be incremented at one or more of the following transitions: at a transition from 0V to 2V, at a transition from 3V to 5V, and/or at a transition from 0V to 5V, and the pullback digital counter operates to be incremented at one or more of the following transitions: at a transition from 0V to 3V, at a transition from 2V to 5V, and/or at a transition from 0V to 5V; and/or (vi) using the data acquisition processor having the ADC, the demodulator, and the rotation digital counter and the pullback digital counter included in the data acquisition processor.

In one or more methods, the one or more processors further include a data acquisition processor operating to acquire the imaging data obtained by the imaging apparatus or system; and the one or more processors include a synchronization processor, and the system further includes a first encoder signal that operates to be available to the rotary motor controller and a second encoder signal that operates to be available to the pullback motor controller, wherein the synchronization processor operates to condition or control the first and second encoder signals before the synchronization processor interfaces with the data acquisition processor such that each time a depth scan is acquired on the imaging data input, information from the encoder signals is recorded for each of the rotary motor and the pullback motor to record an exact or approximate beam position for the depth scan, and the synchronization processor operates to use a single synchronization signal for the data acquisition processor to capture a position of the catheter or probe for each measured depth scan profile, wherein the method(s) may further include one or more of the following: (i) triggering, via a trigger signal, a single acquisition of a depth scan and recording a value of a rotation digital counter and a pullback digital counter derived from a demodulated encoded synchronization signal that is demodulated with a demodulator of the system and/or of the data acquisition processor of the system; (ii) triggering, via a trigger signal, a single acquisition of a depth scan on an analog-to-digital converter (ADC) and recording a rotation digital counter and a pullback digital counter derived from a demodulated encoded synchronization signal that is demodulated with a demodulator of the system and/or of the data acquisition processor of the system; (iii) triggering, via the trigger signal being an A-line trigger signal, a sampling of the imaging data, or triggering, via the trigger signal being a k-clock trigger signal, a sampling of the imaging data so as to uniformly acquiring the imaging data in k space; and/or (iv) using the synchronization signal including or comprising resultant pulse trains which are pulse trains coming from the synchronization processor, wherein the synchronization processor operates to send a pulse corresponding to an index of the first encoder signal which occurs per rotation of the rotary motor except the synchronization processor modifies the pulse at a predetermined or set portion of the pullback, the predetermined or set portion of the pullback being one or more of the following: a start of the pullback where the synchronization processor modifies the pulses in such a way that the synchronization processor blanks or skips one pulse at the start of the pullback, an end of the pullback where the synchronization processor modifies the pulses in such a way that the synchronization processor blanks or skips one pulse at an end of the pullback, a start and an end of the pullback where the synchronization processor modifies the pulses in such a way that the synchronization processor blanks or skips one pulse at the start of the pullback and then another pulse at the end of the pullback, a start and/or an end of the pullback where the synchronization processor modifies the pulse in such a way that the synchronization processor introduces extra pulses and/or delays at the start of the pullback and/or at the end of the pullback, at an end of the pullback where the synchronization processor modifies the pulse to increment a frame counter of the data acquisition processor at a slower rate as the rotary motor is decelerating, and/or at a start of the pullback where the synchronization processor modifies the pulse to increment a frame counter of the data acquisition processor towards a steady rate as the rotary motor accelerates to a steady state target.

One or more method embodiments may involve or have one or more of the following conditions: (i) the data acquisition processor includes a frame counter that is incremented at a fixed, stable, or predetermined or set rate, except at a start of a pullback where the frame counter increments at about half of the predetermined or set rate or at a portion of the predetermined or set rate such that a jump between the start of the pullback and a time when the frame counter is incremented at the fixed, stable, or predetermined or set rate signals or indicates the start and/or the end of the pullback accurately and deduces an approximate or accurate recording of an exact beam position for each depth scan in a case where total pullback length and/or time is known or set; (ii) the one or more processors include a control processor that operates to control, or send commands to, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns, and the data acquisition processor includes a frame counter that is incremented at a fixed, stable, or predetermined or set rate, except, in a case where at an end of the pullback where the synchronization processor modifies the pulse to increment at a slower rate as the rotary motor is decelerating, the first encoder signal pulse trains are delayed further and the frame counter is incremented at an ever increasing number of A-line triggers, the rotary motor deceleration being controlled by the control processor or the one or more processors to coincide with the end of the pullback accurately to reduce or remove uncertainty between the end of the pullback and the start of the rotary motor deceleration and to determine the end of the pullback accurately and deduce the approximate or accurate recording of the exact beam position for each depth scan for a predetermined or set total pullback length and/or time; (iii) the rotary motor has a sharp deceleration profile and the rotary motor operates to decelerate significantly or substantially in one rotation for the number of A-line triggers occurring before the frame counter is incremented such that the deceleration profile of the rotary motor is large enough to be detected as the rotary motor slowing down rather than be detected as a variation in rotary motor rotation speed; and/or (iv) a variation in rotary motor speed operates to lead in normal operation to a pulse train every predetermined or set number of A-line triggers and the rotary motor deceleration during the time equivalent of one steady state rotation operates to be a number of A-line triggers that is larger than the predetermined or set number of A-line triggers such that a threshold value operates to be set or selected above A-line triggers and a threshold value operates to be set or selected below A-line triggers to detect the end of the pullback.

In one or more embodiments, the method(s) may further include one or more of the following: (i) determining, via a pullback status processor of the one or more processors, a pullback status indicating or detecting the start and/or the end of the pullback; (ii) initiating the deceleration of the rotary motor by the rotary motor controller and/or by the rotary motor controller and a driver, wherein the rotary motor controller and/or the driver operate to receive a command to control deceleration from the pullback status processor; (iii) receiving, via the pullback status processor, information from the rotary motor controller and/or the driver to determine the pullback status; and/or (iv) using the pullback status processor while the pullback status processor is disposed or is included in the scanning mechanism of the system.

In one or more embodiments, one or more of the following may occur: (i) the rotary motor is rotated at a velocity that is lower than a target steady state value, and then accelerated at or about the same time as the pullback motor is accelerated; (ii) the data acquisition processor includes a frame counter that is incremented at a fixed, stable, or predetermined or set rate once or as the rotary motor accelerates to the target steady state value; (iii) the one or more processors include a control processor that operates to control, or send commands to, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns, and the rotary motor acceleration is controlled by the control processor or the one or more processors to coincide with the start of the pullback accurately to reduce or remove uncertainty between the start of the pullback and the start of the rotary motor acceleration and to determine the start of the pullback accurately and deduce the approximate or accurate recording of the exact beam position for each depth scan for a predetermined or set total pullback length and/or time; (iv) the rotary motor has a sharp acceleration profile and the rotary motor operates to accelerate significantly or substantially in one rotation for the number of A-line triggers occurring before the frame counter is incremented such that the acceleration profile of the rotary motor is large enough to be detected as the rotary motor speeding up to the target steady state value rather than be detected as a variation in rotary motor rotation speed; and/or (v) a variation in rotary motor speed pre-pullback operates to lead to a pulse train every predetermined or set number of A-line triggers and the rotary motor acceleration during the time equivalent of one steady state rotation operates to be a number of A-line triggers that is larger than the predetermined or set number of A-line triggers such that a threshold value operates to be set or selected to detect the start of the pullback.

One or more method embodiments may further include one or more of the following: (i) determining, via a pullback status processor of the one or more processors, a pullback status indicating or detecting the start and/or the end of the pullback; (ii) initiating the acceleration of the rotary motor by the rotary motor controller and/or by the rotary motor controller and a driver, wherein the rotary motor controller and/or the driver operate to receive a command for controlling the acceleration from the pullback status processor; (iii) receiving, via the pullback status processor, information from the rotary motor controller and/or the driver to determine the pullback status; and/or (iv) using the pullback status processor while the pullback status processor is disposed or is included in the scanning mechanism of the system.

In one or more embodiments, a computer-readable storage medium may store at least one program that operates to cause one or more processors to execute a method for performing image synchronization for one or more imaging modalities of a system, the method comprising: using one or more imaging modalities to obtain imaging data using an imaging apparatus or system of the system; performing beam scanning, via a scanning mechanism of the system, of a catheter or probe of the system to obtain a beam position of the catheter or probe; and achieving image synchronization, via one or more processors of the system, by recording the beam position simultaneously or contemporaneously with the imaging data and enabling accurate spatial registration of the imaging data.

It is at least one broad object of the present disclosure to provide one or more optical apparatuses, systems, methods (for using and/or manufacturing) and storage mediums, such as, but not limited to, fiber optic catheters, endoscopes and/or optical coherence tomography (OCT) apparatuses and systems, and methods and storage mediums, for use with same, to achieve consistent, reliable image synchronization, including at a high efficiency, and at a reasonable cost of manufacture and maintenance.

In one or more embodiments, a computer-readable storage medium may store at least one program that operates to cause one or more processors to execute a method for performing image synchronization, where the method may include one or more steps discussed herein.

In accordance with one or more embodiments of the present disclosure, apparatuses and systems, and methods and storage mediums for performing image synchronization may further operate to characterize biological objects, such as, but not limited to, blood, mucus, tissue, etc.

It should be noted that one or more embodiments of the method(s) for image synchronization, and/or other methods, of the present disclosure may be used in other imaging systems, apparatuses or devices, where images are formed from signal reflection and scattering within tissue sample(s) using a scanning probe. For example, IVI modalities, such as IVUS, may be used where IVI or IVUS images may be processed in addition to or instead of OCT images.

One or more embodiments of the present disclosure may be used in clinical application(s), such as, but not limited to, intervascular imaging, atherosclerotic plaque assessment, cardiac stent evaluation, balloon sinuplasty, sinus stenting, arthroscopy, ophthalmology, ear research, veterinary use and research, etc.

In accordance with at least another aspect of the present disclosure, one or more technique(s) discussed herein may be employed to reduce the cost of at least one of manufacture and maintenance of the one or more apparatuses, devices, systems and storage mediums by reducing or minimizing a number of optical components and by virtue of the efficient techniques to cut down cost of use/manufacture of such apparatuses, devices, systems and storage mediums.

According to other aspects of the present disclosure, one or more additional devices, one or more systems, one or more methods and one or more storage mediums using, or for use with, one or more image synchronization techniques are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE PRESENT DISCLOSURE

One or more devices/apparatuses, optical systems, methods, and storage mediums for performing one or more image synchronization techniques are disclosed herein.

Figure 1:
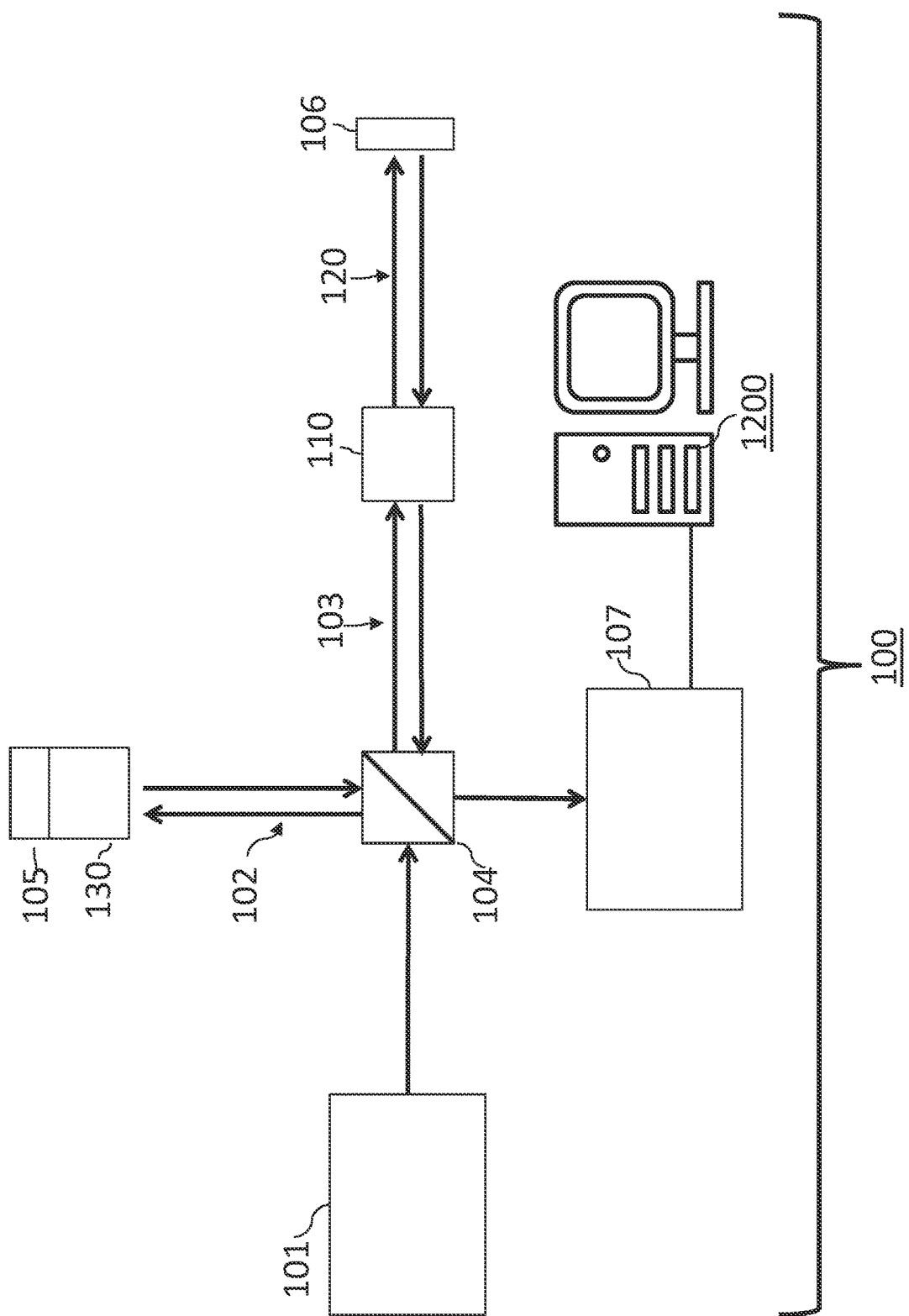
FIG. 1 is a diagram showing an embodiment of a system which can utilize one or more image synchronization techniques in accordance with one or more aspects of the present disclosure.

Turning now to the details of the figures, FIG. 1 shows an OCT system 100 (as referred to herein as "system 100" or "the system 100") which operates to utilize an OCT technique, including, but not limited to, one or more embodiments of image synchronization techniques discussed herein, with optical probe applications in accordance with one or more aspects of the present disclosure. The system 100 comprises a light source 101, a reference arm 102, a sample arm 103, a splitter 104 (also referred to herein as a "beam splitter"), a reference mirror (also referred to herein as a "reference reflection") 105, and one or more detectors 107. The system 100 may include a phase shift device or unit 130, and, in one or more embodiments, the phase shift device or unit may be omitted. In one or more embodiments, the system 100 may include a patient interface device or unit ("PIU") no and a catheter 120 (as diagrammatically shown in FIGS. 1-2), and the system 100 may interact with a sample or target 106 (e.g., via the catheter/probe 120 and/or the PIU 110). In one or more embodiments, the system 100 includes an interferometer, or an interferometer is defined by one or more components of the system 100, such as, but not limited to, at least the light source 101, the reference arm 102, the sample arm 103, the splitter 104, and the reference mirror 105.

The light source 101 operates to produce a light to the splitter 104, which splits the light from the light source 101 into a reference beam passing into the reference arm 102 and a sample beam passing into the sample arm 103. The beam splitter 104 is positioned or disposed at an angle to the reference mirror 105, the one or more detectors 107 and to the sample or target 106. The reference beam goes through the phase shift unit 130 (when included in a system, as shown in the system 100), and the reference beam is reflected from the reference mirror 105 in the reference arm 102 while the sample beam is reflected or scattered from a sample 106 through the PIU (patient interface unit; also referred to herein as a patient interface component (PIC)) no and the catheter 120 in the sample arm 103. Both of the reference and sample beams combine (or recombine) at the splitter 104 and generate interference patterns. The output of the system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 1200, 1200' (shown in FIG. 13 or FIG. 14, respectively, discussed further below). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

The light source 101 may include a plurality of light sources or may be a single light source. The light source 101 generates broadband laser lights in one or more embodiments. The light source 101 may include one or more of a laser, an organic Light-Emitting Diode (OLED), a Light-Emitting Diode (LED), a halogen lamp, an incandescent lamp, supercontinuum light source pumped by a laser, and/or a fluorescent lamp. The light source 101 may be any light source that provides light which can then be split up into at least three bands in which each band is further dispersed to provide light which is then used to for spectral encoding of spatial information. The light source 101 may be fiber coupled or may be free space coupled to the other components of the system or systems discussed herein, such as, but not limited to, the system 100, the system 100a, the system 100', the system 100", the system 100''', etc.

In accordance with at least one aspect of the present disclosure, a feature of OCT systems is implemented using fiber optics. As aforementioned, one application of an OCT technique of the present disclosure is to use OCT with a catheter 120 as schematically shown in FIGS. 1-2.

Figure 2:
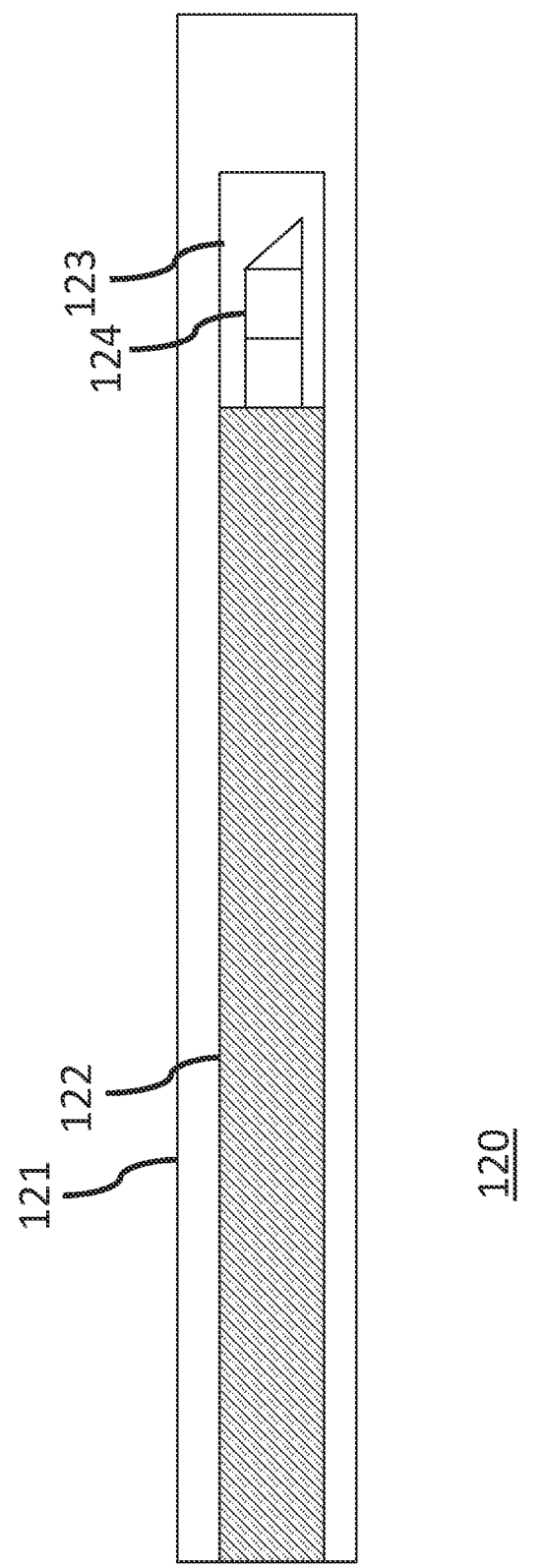
FIG. 2 is a diagram of an embodiment of a catheter that may be used with at least one embodiment of an apparatus or system for performing image synchronization techniques in accordance with one or more aspects of the present disclosure.

FIG. 2 shows an embodiment of the catheter 120 including a sheath 121, a coil 122, a protector 123 and an optical probe 124. As shown schematically in FIGS. 1-2, the catheter 120 preferably is connected to the PIU 110 to spin the coil 122 with pullback (e.g., at least one embodiment of the PIU 110 operates to spin the coil 122 with pullback). The coil 122 delivers torque from a proximal end to a distal end thereof (e.g., via or by a rotational motor in the PIU 110). In one or more embodiments, the coil 122 is fixed with/to the optical probe 124 so that a distal tip of the optical probe 124 also spins to see an omnidirectional view of a biological organ, sample or material being evaluated, such as, but not limited to, hollow organs such as vessels, a heart, etc. For example, fiber optic catheters and endoscopes may reside in the sample arm (such as the sample arm 103 as shown in FIG. 1) of an OCT interferometer in order to provide access to internal organs, such as intravascular images, gastrointestinal tract or any other narrow area, that are difficult to access. As the beam of light through the optical probe 124 inside of the catheter 120 or endoscope is rotated across the surface of interest, cross-sectional images of one or more samples are obtained. In order to acquire three-dimensional data, the optical probe 124 is simultaneously translated longitudinally during the rotational spin resulting in a helical scanning pattern. This translation may be performed by pulling the tip of the probe 124 back towards the proximal end and therefore referred to as a pullback.

In one or more embodiments, the patient user interface no may comprise or include a connection component (or interface module), such as a rotary junction, to connect one or more components, such as one or more components of a probe (e.g., a catheter 120 (see e.g., FIGS. 1-2)), a needle, a capsule, a patient interface unit or component (e.g., the patient interface unit or component no), etc., to one or more other components, such as, an optical component, a light source (e.g., the light source 101), a deflection section (e.g., such as the deflection or deflected section, which is a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc.), the sample arm 102, a motor that operates to power the connection component and/or the patient user interface no, etc. For example, when the connection member or interface module is a rotary junction, preferably the rotary junction operates as discussed below). In one or more other embodiments, the rotary junction may be at least one of: a contact rotary junction, a lenseless rotary junction, a lens-based rotary junction, or other rotary junction known to those skilled in the art.

In at least one embodiment, the PIU 110 may include a Fiber Optic Rotary Junction (FORJ), a rotational motor and translation motorized stage (e.g., a portion of the PIU 110), and a catheter connector (e.g., a portion of the PIU 110). The FORJ allows uninterrupted transmission of an optical signal while rotating a fiber along the fiber axis. The FORJ may have a free space optical beam combiner including a rotor and stator.

At least one embodiment of an imaging system or device in accordance with one or more features of the present disclosure was prototyped to investigate the feasibility of synchronizing acquisition of images with probe location for the entire probe scanning. The probe in at least one embodiment may be a catheter with a fixed outer sheet and a rotatable and translatable inner core including an optical fiber and distal optics to focus light on a sample.

Volumetric images of luminal organs like coronary arteries may be obtained by rapidly rotating and simultaneously translating the inner core of the catheter to obtain cross-sectional images. One or more embodiments of the system or device may include an imaging system, an imaging catheter, and a Patient Interface Unit (PIU). The PIU (e.g., the PIU 110, any other PIU discussed herein, etc.) may be used to scan the catheter core so that a beam delivered and recovered by the imaging catheter may then be recovered by the system or device to generate images of the luminal organ.

Figure 3:
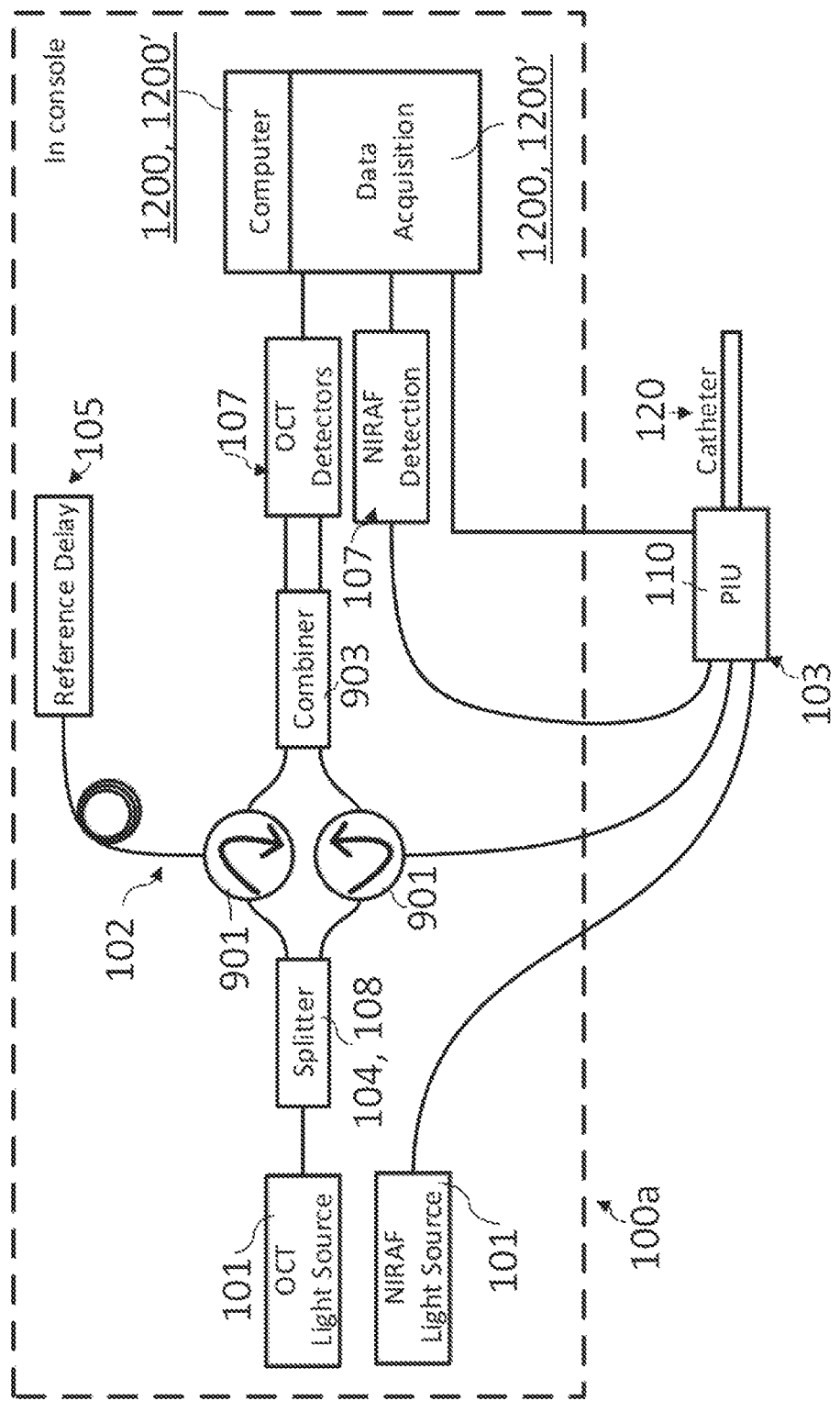
FIG. 3 is a diagram showing at least one apparatus/system embodiment for performing image synchronization techniques in accordance with one or more aspects of the present disclosure.

FIG. 3 shows a general schematic diagram of at least one embodiment according to the present disclosure which may include a multi-modality swept source optical coherence tomography and laser induced near infrared auto-fluorescence system. The system may also be single modality OCT, OFDI, any other imaging modality discussed herein, etc., or the system may use a different second modality like near infrared spectroscopy or other modality. The system 100a may include an OCT light source 101, a NIRF or NIRAF light source 101, a beam splitter 104, 108, one or more circulators 901, a reference arm 102 including a reference reflection 105 (which may or may not include a reference delay portion of the reference arm 102), a combiner 903, OCT detector(s) 107, a NIRF and/or NIRAF detector(s) 107, a computer and/or data acquisition unit (such as, but not limited to, a computer 1200, a computer 1200', any other processor or computer discussed herein, etc.), and a sample arm including the PIU 110 and the catheter 120. The light from the imaging system 100a may be directed to the PIU 110 and imaging catheter 120 along the sample arm 103, and then may be passed through the OCT detector(s) 107 and/or the NIRF and/or NIRAF detector(s) 107.

Figure 4:
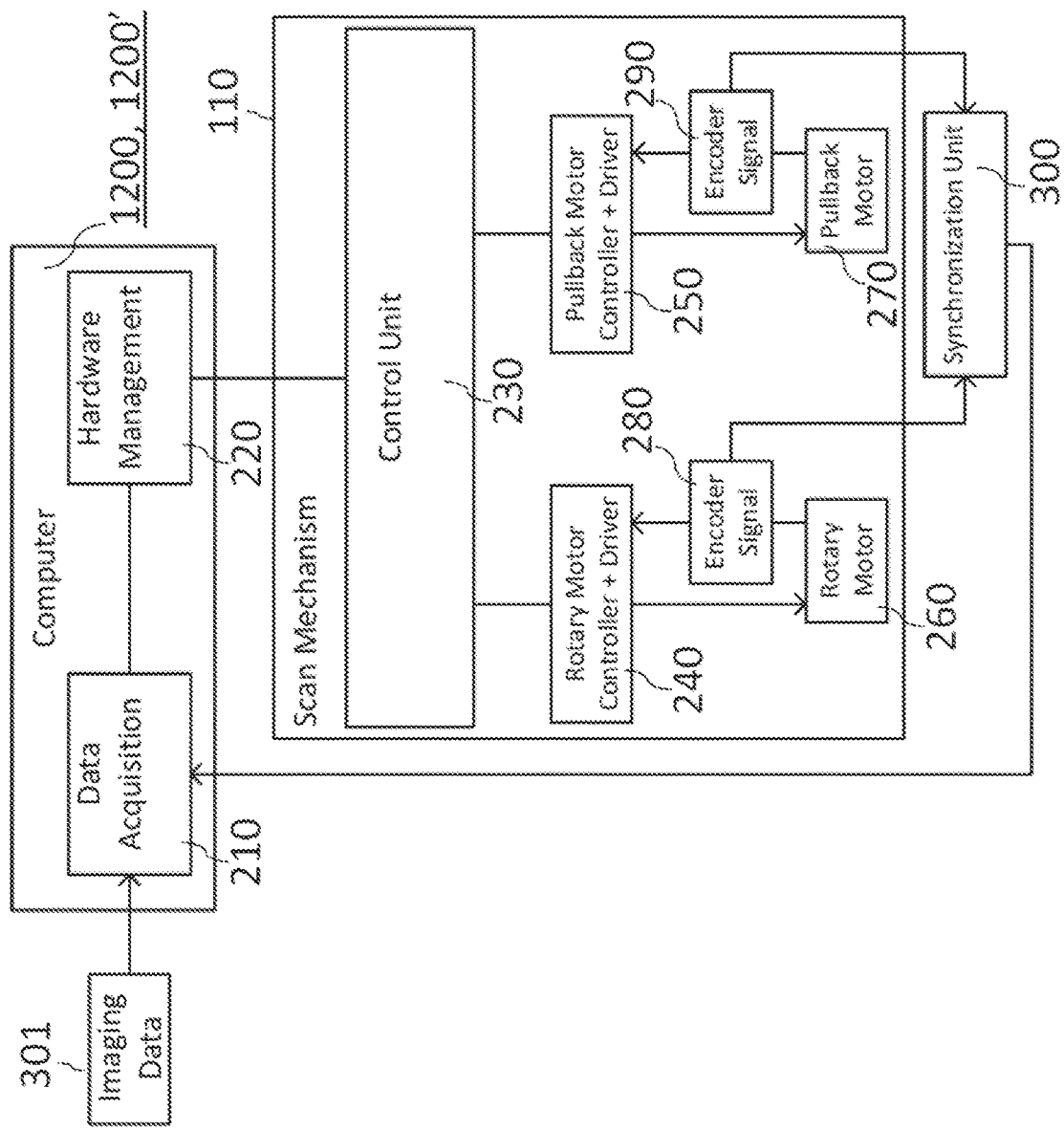
FIG. 4 is a diagram showing at least one embodiment of an apparatus or system for performing image synchronization techniques in accordance with one or more aspects of the present disclosure.

FIG. 4 shows at least one embodiment of a block and flow diagram of signals and imaging data connections between elements of a data acquisition processor or unit 210 and a hardware management processor or unit 220, and the PIU scan mechanism no and synchronization unit 300. In one or more embodiments, the scan mechanism may be included or may be a portion of the PIU 110. The synchronization unit 300 operates to allow the beam position to be simultaneously recorded with imaging data (e.g., from and/or stored in an imaging data unit 301), enabling accurate spatial registration of the imaging data. The imaging data obtained by the imaging system may be acquired by a data acquisition processor or unit 210 under control of the hardware management processor or unit 220. The catheter 120 beam scanning may be performed by the scanning mechanism enclosed in the PIU 110 using a motor 260 for rotation (e.g., a rotary motor 260) and a motor 270 for pullback (e.g., a pullback motor 270). Each motor 260, 270 may be controlled, respectively, by a motor controller and driver 240, 250. A control unit or processor 230 may be included in the PIU 110 and may be in charge of commanding each motor controller 240, 250 to achieve certain desired velocities and/or positions to yield certain desired scan patterns. Respective encoder signals 280, 290 may be configured to be available to the motor controller units 260, 270 and the synchronization processor or unit 300. In one or more embodiments, the encoder signals 280, 290 may be conditioned by the synchronization unit 300 before interfacing the synchronization processor or unit 300 with the data acquisition unit 210 such that each time a depth scan is acquired on the imaging data input or received via the catheter 120, information from the encoder signals 280, 290 may be recorded for each respective motor 260, 270 to approximately and accurately record the exact beam position for that depth scan.

Figure 5:
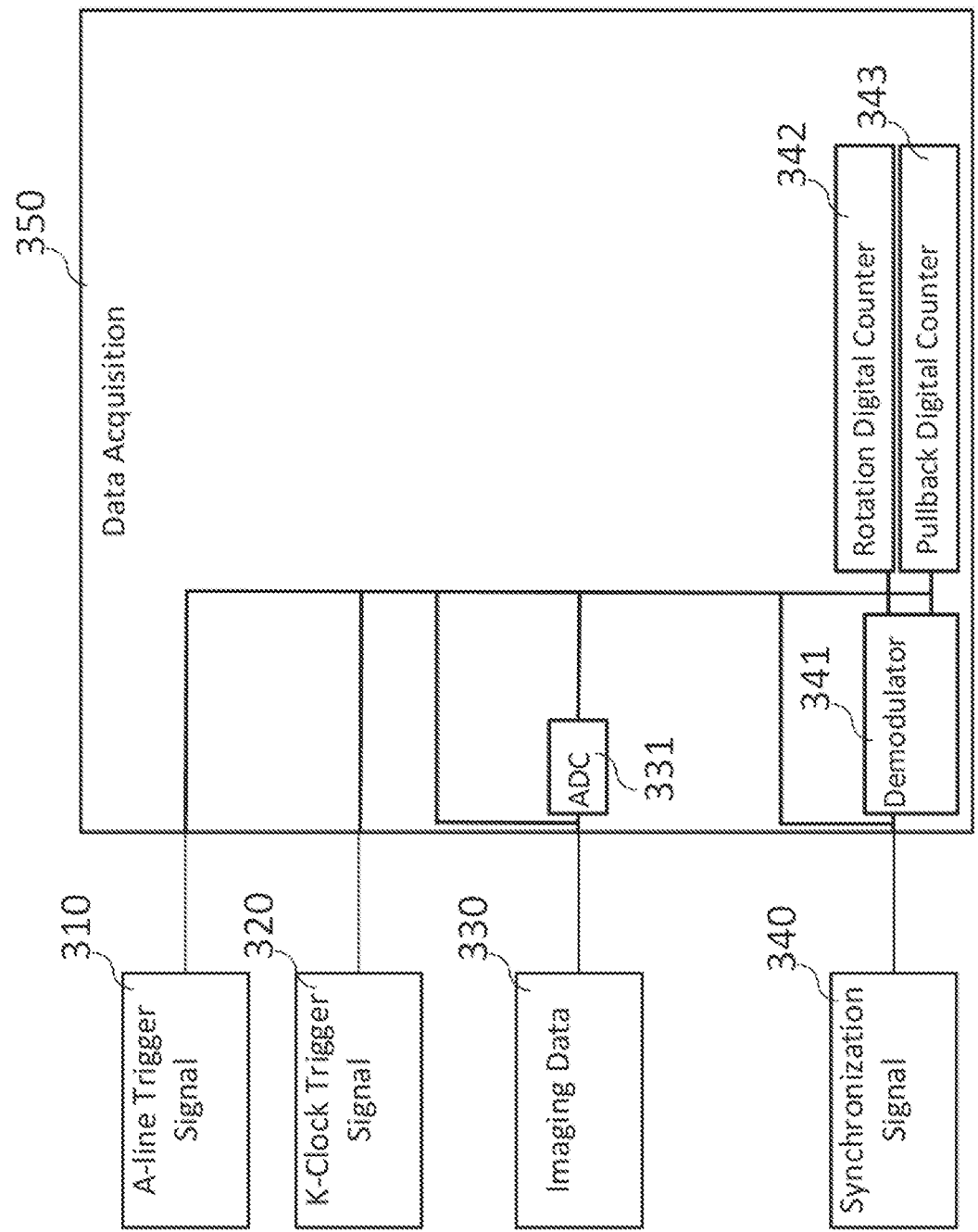
FIG. 5 is a diagram showing at least one embodiment of an apparatus or system using a synchronization signal for data acquisition to capture a probe position for each measured depth profile in accordance with one or more aspects of the present disclosure.

One or more embodiments (e.g., as shown in FIG. 5) may utilize a single synchronization signal for the data acquisition unit 210 to capture probe position for each measured depth profile. For example, an A-line trigger signal 310 may be used to trigger a single acquisition of a depth scan on an analog to digital converter (ADC) 331, and also to record the value of digital counters (e.g., a rotational digital counter 342 and a pullback digital counter 343) derived from a demodulated encoded synchronization signal 340 that is demodulated with a demodulator 341 of the data acquisition processor or unit 350 (In one or more embodiments, the data acquisition processor or unit 350 may be in or part of the data acquisition processor or unit 210). For example, a k-clock trigger signal 320 may be used to trigger the sampling of the imaging data 330 (and/or the imaging data 301) so as to uniformly acquire the imaging data in k space. The synchronization signal 340 may be resultant pulse trains which may be the result or resultant of superimposition of pulse trains from each of the two encoder signals 280, 290 that may switch at a defined rate per motor revolution. The encoder signal pulses may have, in one or more embodiments, a 2V amplitude for the rotary encoder signal and a 3V amplitude for the pullback signal. Thus, the rotation digital counter may be incremented at a transition from any one of: from 0V to 2V, from 3V to 5V, or from 0V to 5V, and the pullback digital counter may be incremented at a transition from any one of: from 0V to 3V, from 2V to 5V, or from 0V to 5V. By counting these switches using the digital counters, the current motor positions may be measured. The ADC converter 331, the demodulation unit 341, and the digital counters 342, 343 may be contained in the data acquisition unit 350.

Figure 6:
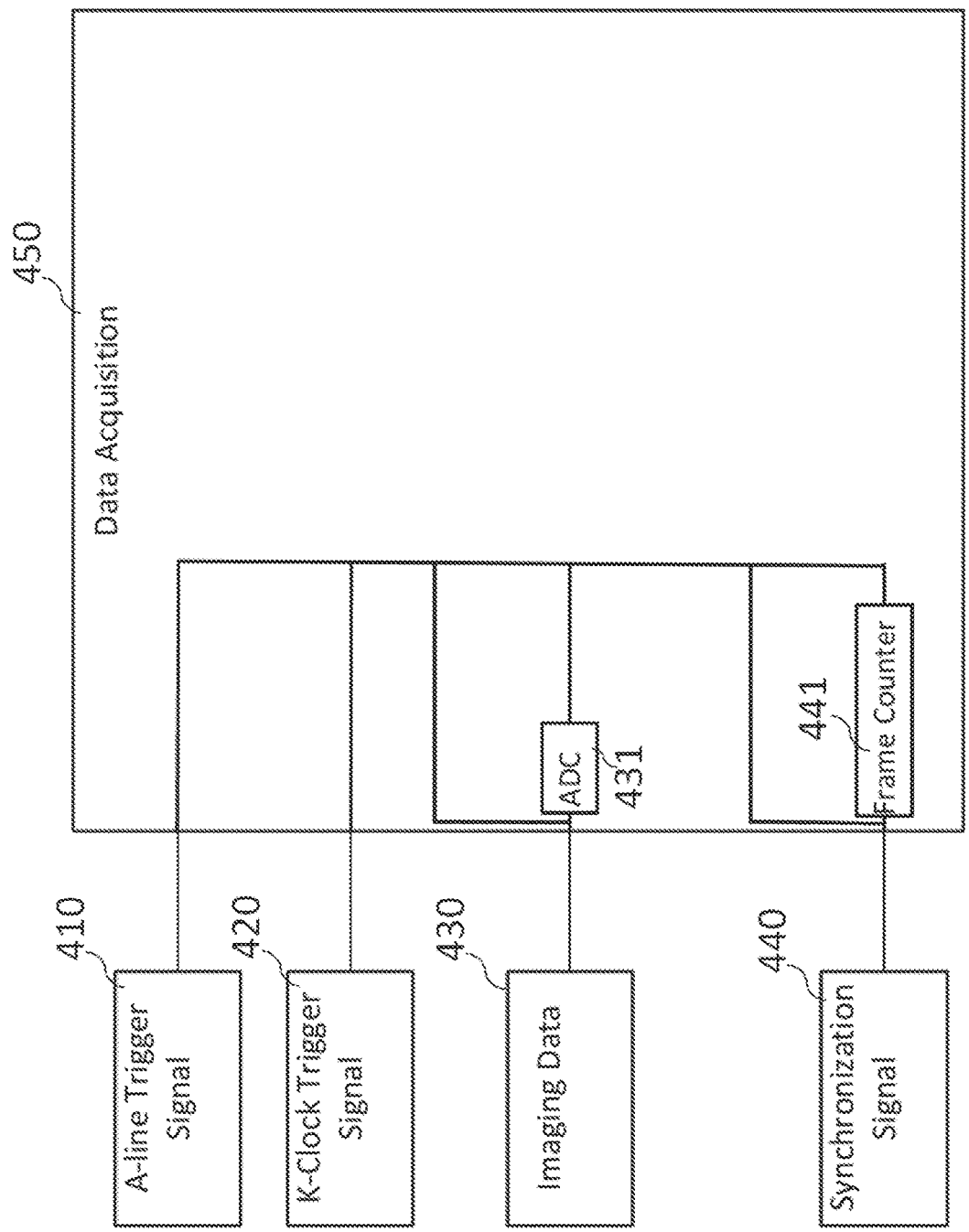
FIG. 6 is a diagram showing at least an additional embodiment of an apparatus or system using a synchronization signal for data acquisition to capture a probe position for each measured depth profile in accordance with one or more aspects of the present disclosure.

FIG. 6 shows at least one embodiment of the present disclosure in which a single synchronization signal may be utilized for the data acquisition processor or unit 210 to capture probe position for each measured depth profile. For example, a trigger signal 410 may be used to trigger a single acquisition of a depth scan on an analog to digital converter (ADC) 431, and also to record the value of a frame counter 441 derived from the synchronization signal 440 input for each acquired depth scan. For example, a k-clock trigger signal 420 may be used to trigger the sampling of the imaging data (e.g., from the imaging data 430) so as to uniformly acquire the imaging data in k space. The synchronization signal 440 may be resultant pulse trains which are pulse trains coming from the synchronization processor or unit 300. In one or more embodiments, the synchronization processor or unit 300 operates to send a pulse corresponding to the index of the encoder signal 280 which may occur per rotation of the rotary motor 260, except, in one or more embodiments, at the start of the pullback where the synchronization processor or unit 300 modifies the pulses in such a way that the synchronization processor or unit 300 blanks (for example, the synchronization processor or unit 300 may blank by skipping one pulse at the start of the pullback). In one or more embodiments, the rotary motor (e.g., the rotary motor 260) rotates at mostly stable speed, for example, one rotation every 500 A-line triggers. In one or more embodiments, the frame counter 441 is incremented at a relatively stable rate of, for example, once every 500 A-line triggers, except, in one or more embodiments, at a start of a pullback where the frame counter 441 may increment at about half the original rate or after about 1,000 A-line triggers. This jump may be used to determine a start of a pullback accurately and, therefore, deduce the approximate recording of the exact beam position for that depth scan assuming that the total pullback length/time is known or set a priori or beforehand.

In another embodiment, the synchronization processor or unit 300 may work to send a pulse corresponding to the index of the encoder signal 280 which may occur per rotation of the rotary motor 260, except, in one or more embodiments, at the end of the pullback where the synchronization processor or unit (e.g., the synchronization processor or unit 300) may modify the pulses in such a way that the synchronization processor or unit 300 blanks (for example, the synchronization processor or unit 300 may blank by skipping one pulse at the end of the pullback). This jump may be used to determine an end of a pullback accurately and, therefore, deduce the approximate or accurate recording of the exact beam position for that depth scan assuming that the total pullback length/time is known a priori or beforehand.

In one or more other embodiments, the synchronization processor or unit 300 may work to send a pulse corresponding (for example, the synchronization processor or unit 300 may blank by skipping one pulse at the end of the pullback) to the index of the encoder signal 280 which may occur per rotation of the rotary motor 260, except at the start and at the end of the pullback where the synchronization processor or unit 300 modifies the pulses in such a way that the synchronization processor or unit 300 blanks (for example, the synchronization processor or unit 300 may blank by skipping one pulse at the start of the pullback and another pulse at the end of the pullback). These two jumps may be used to determine a start and an end of a pullback accurately and, therefore, deduce the approximate or accurate recording of the exact beam position for that depth scan. In one or more embodiments, a priori or beforehand knowledge of total pullback length/time may be used or may not be used.

In one or more other embodiments, the synchronization processor or unit 300 may work to send a pulse corresponding to the index of the encoder signal 280 which may occur per rotation of the rotary motor 260, except at the start and or at the end of the pullback where the synchronization processor or unit 300 modifies the pulses in such a way that, instead of blanking, the synchronization processor or unit 300 introduces extra pulses and/or delays pulses at either the start of the pullback and/or the end of the pullback. The jumps in the number of A-line triggers for the frame counter 441 to be incremented may be used to determine start of and/or end of pullback accurately and, therefore, deduce the approximate recording of the exact beam position for that depth scan.

In one or more further embodiments, the synchronization signal 440 may be resulting or resultant pulse trains which are pulse trains coming from the synchronization processor or unit 300. In one or more embodiments, the synchronization processor or unit 300 may work to send a pulse corresponding to the index of the encoder signal 280 which may occur per rotation of the rotary motor (e.g., the rotary motor 260). In one or more embodiments, the rotary motor (e.g., the rotary motor 260) may rotate at a mostly stable speed, for example, one rotation every 500 A-line triggers. In one or more embodiments, the frame counter 441 may be incremented at a relatively stable rate of, for example, once every 500 A-line triggers, except at an end of pullback where the frame counter 441 may be incremented at a slower rate as the rotary motor 260 is decelerating. In one or more embodiments, as the rotary motor (e.g., the rotary motor 260) is decelerating, the encoder signal 280 pulse trains may be delayed further, and the frame counter 441 may be incremented at a predetermined increasing number of A-line triggers or at an ever increasing number of A-line triggers. Deceleration may be commanded by the control processor or unit 230 to coincide with an end of a pullback accurately to reduce uncertainty between the end of the pullback and a start of rotary motor deceleration. This slowing down of the frame counter 441 incrementing may be used to determine the end of the pullback accurately and, therefore, may deduce the approximate recording of the exact beam position for that depth scan assuming that the total pullback length/time is known a priori or beforehand. In one or more embodiments, the rotary motor 260 may have a sharp deceleration profile such that the rotary motor 260 may decelerate significantly in one rotation for the number of A-line triggers occurring before the frame counter 441 is incremented such that the deceleration profile of the rotary motor 260 is large enough to be detected as the rotary motor 260 slowing down rather than be detected as a variation in rotary motor rotation speed. For example, the variation in motor speed may lead in normal operation to a pulse train every 500±2 A-line triggers, but the motor deceleration during the time equivalent of one steady state rotation may be at least 510 A-line triggers in one or more embodiments. As such, a threshold value may be selected above a predetermined number of A-line triggers and below another predetermined number of A-line triggers, such as, but not limited to, above 502 and below 510 A-line triggers to detect an end of a pullback.

In one or more other embodiments, the synchronization processor or unit 300 may work to send a pulse corresponding to the index of the encoder signal 280 which may occur per rotation of the rotary motor 260. The rotary motor 260 in at least one embodiment may be rotating at a velocity, such as, but not limited to, 490 A-line triggers per rotation or any other set or predetermined number of A-line triggers per rotation which is lower than the target steady state value of one rotation every 500 A-line triggers or any other set or predetermined target steady statue value of a certain number of rotation(s) every set number of A-line triggers. The rotary motor (e.g., the rotary motor 260, the rotary motor 560 of FIG. 7, etc.) may then be accelerated at or about the same time as the pullback motor is (e.g., the pullback motor 270, the pullback motor 570 of FIG. 7, etc.). In this case, the start of a pullback may be determined as soon as the frame counter 441 is incremented at a relatively stable rate of, for example, once every 500 A-line triggers (or any other set or predetermined amount per every set or predetermined amount of A-line triggers) as the rotary motor 260 is accelerated to its steady state target (which may be set manually by a user, which may be set automatically by any algorithm, method, or processor or unit, etc. discussed herein, etc.). Acceleration may be commanded by the control processor or unit 230 to coincide with a start of a pullback accurately to reduce uncertainty between the start of the pullback and a start of rotary motor acceleration (e.g., acceleration of the rotary motor 260, acceleration of the rotary motor 560, etc.). This stabilization of frame counter 441 incrementing may be used to determine a start of a pullback accurately and, therefore, may deduce or be used to determine the approximate recording of the exact beam position for that depth scan assuming that the total pullback length/time is known a priori or beforehand. In one or more embodiments, the rotary motor 260 may have a sharp acceleration profile such that the rotary motor 260 may accelerate significantly in one rotation for the number of A-line triggers occurring before the frame counter 441 is incremented such that the acceleration profile of the rotary motor 260 is large enough to be detected as the rotary motor 260 speeding up to a steady state value rather than be detected as a variation in rotary motor rotation speed. For example, the variation in motor speed pre-pullback may lead to a pulse train every 490±2 A-line triggers, but the motor acceleration to steady state pullback speed rotation of 500±2 A-line triggers may always be achieved in a deterministic way preferably in one rotation. As such, a threshold value may be selected to detect start of pullback, and/or a threshold for variation in motor speed pre-pullback or for a steady state pullback speed rotation may be set.

Figure 7:
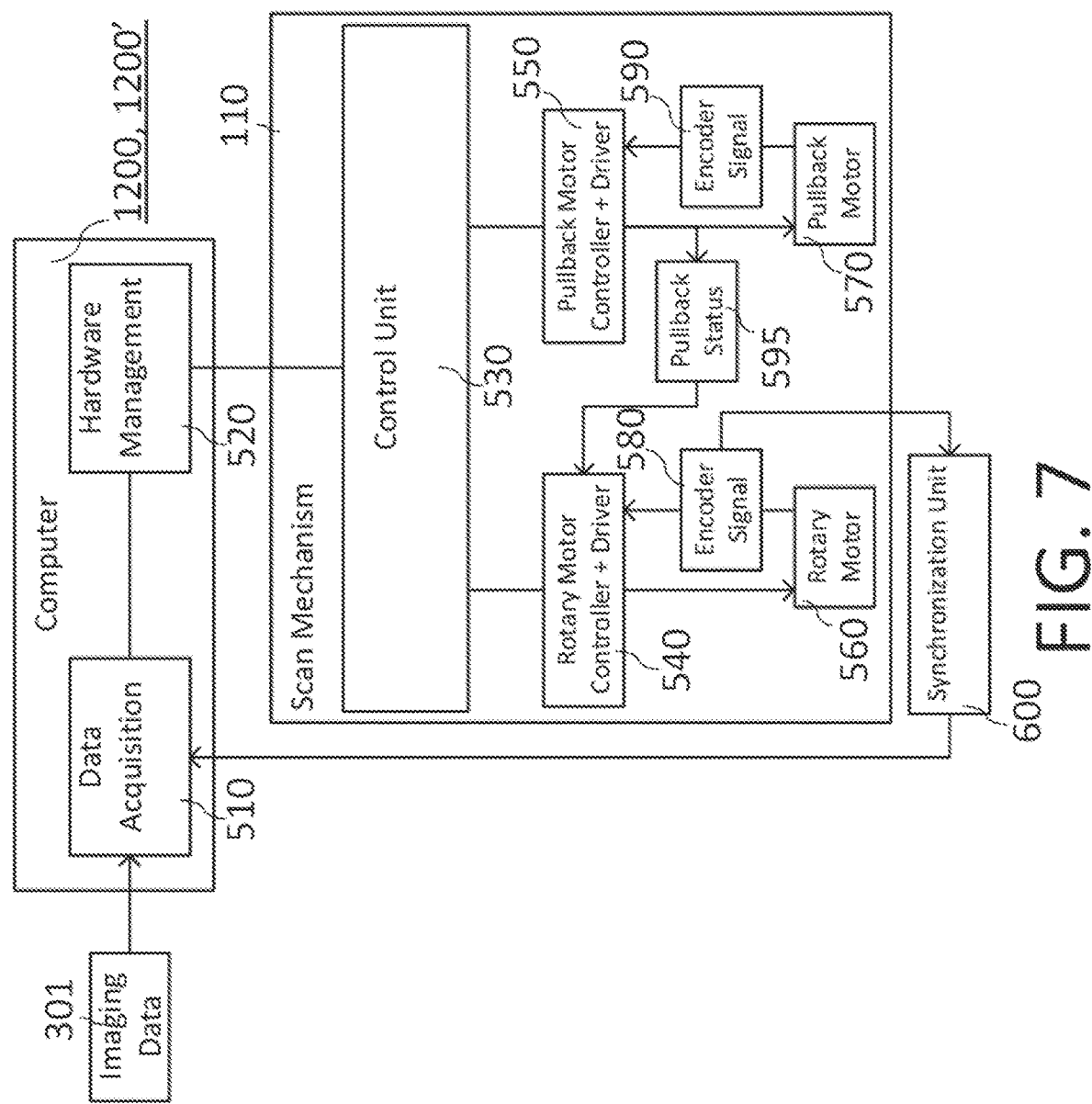
FIG. 7 is a diagram showing at least one embodiment of an apparatus or system using a synchronization technique and using a pullback motor and controller in accordance with one or more aspects of the present disclosure.

In one or more further embodiments, a combination of one or more features of the aforementioned embodiments may be implemented to detect both start and end of a pullback. Variations on one or more of the aforementioned embodiments may be such that the either start of acceleration and or deceleration of the rotary motor 560 may be initiated by the rotary motor controller and driver 540 and may receive its command from the pullback status unit 595 as shown in FIG. 7. The pullback (PB) status processor or unit 595 may determine the pullback status from the pullback motor controller and driver 550 as shown in FIG. 7 or from the encoder signal 590 as shown in FIG. 7. The synchronization processor or unit 600 may be configured to provide signal conditioning or may be bypassed if the encoder signal 580 is fully compatible with the data acquisition unit 510. The structure shown in FIG. 7 may be used with any of the aforementioned features discussed above for FIGS. 1-6 of the present disclosure.

Descriptions of like-numbered elements present in the system 100' and already described above, such as for the system 100 and/or for the system bow, shall not be repeated, and are incorporated by reference herein in their entireties.

Additionally or alternatively, in one or more embodiments where like-named elements have different numbers (e.g., as shown in the embodiments of FIGS. 4 and 7), it is understood that any feature discussed for the differently numbered, like-named elements may be used for one or all of such like-named elements. For example, while FIG. 4 shows the data acquisition processor or unit 210, the hardware management 220, the control processor or unit 230, the rotary motor controller and driver 240, the pullback motor controller and driver 250, the rotary motor 260, the pullback motor 270, the encoder signal 280, the encoder signal 290, and the synchronization processor or unit 300, one or more embodiments of the present disclosure may include, additionally or alternatively, the differently numbered and like-named element(s), such as, but not limited to, the data acquisition processor or unit 510, the hardware management 520, the control processor or unit 530, the rotary motor controller and driver 540, the pullback controller and driver 550, the rotary motor 560, the pullback motor 570, the encoder signal 580, the encoder signal 590, and the synchronization processor or unit 600 as shown in FIG. 7. Indeed, one or more embodiments may include one or more of the following: the data acquisition unit 210 and/or the data acquisition unit 510, the hardware management 220 and/or the hardware management 520, the control processor or unit 230 and/or the control processor or unit 530, the rotary motor controller and driver 240 and/or the rotary motor controller and driver 540, the pullback controller and driver 250 and/or the pullback controller and driver 550, the rotary motor 260 and/or the rotary motor 560, the pullback motor 270 and/or the pullback motor 570, the encoder signal 280 and/or the encoder signal 580, the encoder signal 290 and/or the encoder signal 590, the synchronization processor or unit 300 and/or the synchronization processor or unit 600, etc.

In at least one embodiment, the console 1200, 1200' operates to control motions of a motor and translation motorized stage (hereinafter referred to as "motor" or "motor and stage"), acquires intensity data from the at least one detector(s) 107, and displays the scanned image (e.g., on a monitor or screen such as a display, screen or monitor 1209 as shown in the console 1200 of FIG. 13 and/or the console 1200' of FIG. 14 as further discussed below). In one or more embodiments, the console 1200, 1200' operates to change a speed of the motor and/or to stop the motor. The motor may be a stepping or a DC servo motor to control the speed and increase position accuracy. In one or more embodiments, the console 1200, 1200' may operate to control any of the aforementioned processors or units, controllers and drivers, signals, and/or motors, etc., including, but not limited to: the data acquisition unit 210 and/or the data acquisition unit 510, the hardware management 220 and/or the hardware management 520, the control processor or unit 230 and/or the control processor or unit 530, the rotary motor controller and driver 240 and/or the rotary motor controller and driver 540, the pullback controller and driver 250 and/or the pullback controller and driver 550, the rotary motor 260 and/or the rotary motor 560, the pullback motor 270 and/or the pullback motor 570, the encoder signal 280 and/or the encoder signal 580, the encoder signal 290 and/or the encoder signal 590, the synchronization processor or unit 300 and/or the synchronization processor or unit 600, etc.

In one or more embodiments, the console or computer 1200, 1200' operates to control the system 100 and/or the system 100a (and other systems, such as, but not limited to, the system 100', the system 100", the system 100''', etc. as discussed further below), the catheter 120 and/or one or more other above-described components of the system 100 and/or the system bow. In at least one embodiment, the console or computer 1200, 1200' operates to acquire intensity data from the at least one detector 107 of the OCT system/device/apparatus, and displays the image(s) (e.g., on a monitor or screen such as a display, screen or monitor 1209 as shown in the console 1200 of FIG. 13 and/or the console 1200' of FIG. 14 as further discussed below). The output of the one or more components of the system 100 and/or the system 100*a* (and other systems, such as, but not limited to, the system 100', the system 100", the system 100''', etc. as discussed further below) is acquired with the at least one detector 107 of the OCT system/device/apparatus, e.g., such as, but not limited to, photodiodes, Photomultiplier tube(s) (PMTs), line scan camera(s), or multi-array camera(s). Electrical analog signals obtained from the output of the system 100 and/or the system 100*a* (and/or other systems, such as, but not limited to, the system 100', the system 100", the system 100''', etc. as discussed further below) or one or more components thereof are converted to digital signals to be analyzed with a computer, such as, but not limited to, the computer 1200, 1200' (e.g., as shown in FIGS. 1, 3-7, 9-11, and 13-14). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector 107 comprises three detectors configured to detect three different bands of light.

In one or more embodiments, one or more imaging techniques may be used, such as, but not limited to, various OCT imaging techniques, lumen edge detection, stent strut detection, and/or artifact detection techniques, and other techniques as discussed in at least U.S. Pat. App. No. 62/901,472, which is incorporated by reference herein in its entirety. In one or more embodiments of the present disclosure, an OCT image is formed in a polar coordinate system from A-lines. Each A-line includes much information about the imaged object, such as, but not limited to: clear indications of artifacts from metal objects (e.g., stents, stent struts, guide wires, PIU reflection, catheter/probe reflection, noise artifacts, etc.) like narrow signal width and/or sharp rising and falling edges; significant difference in signal intensity and shape for unobstructed soft tissue compared to the sheath reflection and other artifacts like wide signal width and a gentle falling edge. Each A-line may represent a cross-sectional 1D sampling of a target, sample, object, etc., such as, but not limited to, a vessel, along a certain view angle. As an imaging probe or device rotates (e.g., rotates about 0 to about 360 degrees, about 180 degrees to about 360 degrees, about 360 degrees, etc.), the corresponding A-lines form the complete two-dimensional (2D) cross-section of the target, sample, object, etc. (e.g., the vessel) in polar coordinates, which is then converted into Cartesian coordinates to form the tomographical-view (tomo-view) image of the cross-section of the target, sample, object, etc. (e.g., the vessel).

In accordance with at least one aspect of the present disclosure and as aforementioned, one or more additional methods for lumen, stent, and/or artifacts detection of OCT images are provided herein and are discussed in U.S. patent application Ser. No. 16/414,222, filed on May 16, 2019, the entire disclosure of which is incorporated by reference herein in its entirety.

Regardless of the approach, a predetermined or determined threshold may be used to detect the most significant pulse that may be corresponding to the lumen edge (in one or more embodiments, the most significant pulse denotes the maximum peak and its associated front edge also named as "major peak/edge"; such data may contain or include artifact edge pixels) in a specific A-line in one or more embodiments. Any pulse above the threshold is an edge pulse of an object candidate. The largest pulse among all the candidates in terms of area under the pulse is considered to be the maximum peak (also referred to herein as the "most significant pulse", or the "major peak/edge", etc.).

One or more embodiments of the present disclosure may use an OCT signal and/or a NIRF and/or NIRAF signal (e.g., at a PIU output connector) to determine image synchronization, and/or may use an OCT signal and/or a NIRF and/or NIRAF signal about or for the PIU output connector and a catheter connector to determine image synchronization.

As shown via the reference numbers in FIGS. 1-7, while not limited to such examples, one or more of the subject apparatuses or systems may have the same or similar components (or one or more of the same or similar components) as other apparatuses or systems discussed herein. For example, one or more apparatuses may have a light source 101, a splitter 104 or deflecting section 108, one or more circulators 901, a reference arm 102, a sample arm 103, a PIU 110, a catheter or probe 120, a reference reflector 105, a detector (e.g., a photo-receiver, a photo diode, etc.) 107, a computer, processor or other type of data acquisition unit (DAQ) (e.g., computer or processor 1200, computer or processor 1200', etc.), etc. Numerous non-limiting, non-exhaustive embodiment examples of such components are discussed throughout the disclosure with reference to at least FIGS. 1-7, 9-11, and 13-14, and detail(s) of one or more embodiments of one or more of such components will not be repeated with reference to later discussed figures of the present disclosure.

Figure 8:
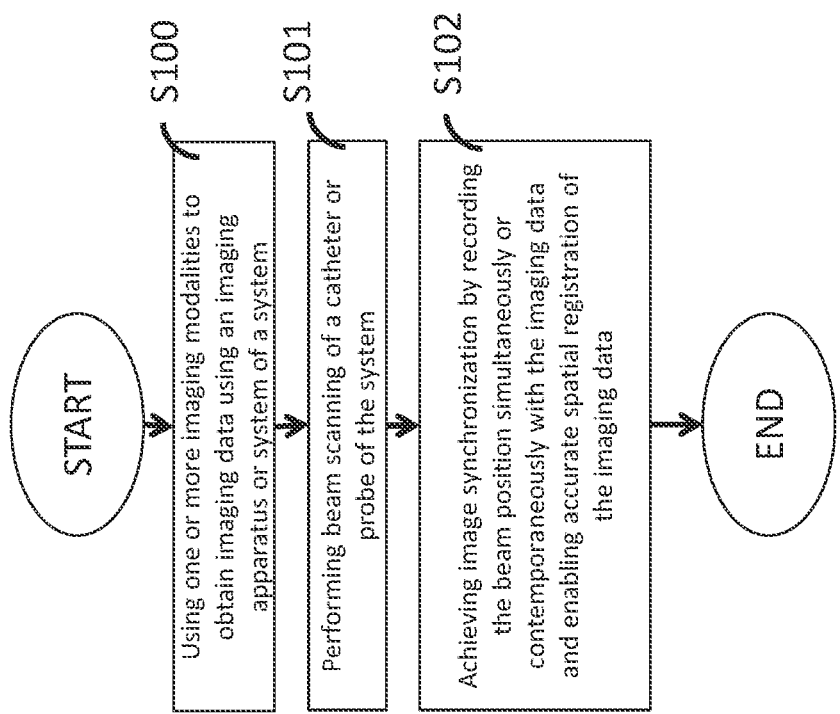
FIG. 8 is a flow chart of at least one embodiment of an image synchronization method or technique in accordance with one or more aspects of the present disclosure.

At least one image synchronization method embodiment of the present disclosure describes steps (e.g., as shown in FIG. 8) that may be used to determine image synchronization. In one or more embodiments, determining image synchronization may include one or more of the following: (i) using one or more imaging modalities to obtain imaging data using an imaging apparatus or system of a system (see e.g., step S100 in FIG. 8); (ii) performing beam scanning of a catheter or probe of the system (e.g., via a scanning mechanism of the system) (see e.g., step S101 in FIG. 8); and (iii) achieving image synchronization by recording the beam position simultaneously or contemporaneously with the imaging data and enabling accurate spatial registration of the imaging data (see e.g., step S102 in FIG. 8). One or more methods may include one or more features of methods discussed herein.

In one or more embodiments, a method for controlling a system for performing image synchronization may include: using one or more imaging modalities to obtain imaging data using an imaging apparatus or system of the system; performing beam scanning, via a scanning mechanism of the system, of a catheter or probe of the system to obtain a beam position of the catheter or probe; and achieving image synchronization, via one or more processors of the system, by recording the beam position simultaneously or contemporaneously with the imaging data and enabling accurate spatial registration of the imaging data.

In one or more embodiments, the method may further include: controlling, via a hardware management processor, a data acquisition processor of the one or more processors, and acquiring, via the data acquisition processor, the imaging data obtained by the imaging apparatus or system.

One or more methods may include: (i) rotating the scanning mechanism, a part of the scanning mechanism, and/or the catheter or probe using a rotary motor, and (ii) controlling a pullback of the catheter or probe using a pullback motor, wherein the catheter or probe beam scanning is performed by the scanning mechanism using the rotary motor and the pullback motor.

One or more methods may include one or more of the following: (i) controlling, via a hardware management processor, a data acquisition processor of the one or more processors; (ii) acquiring, via the data acquisition processor, the imaging data obtained by the imaging apparatus or system; (iii) controlling the rotary motor using a rotary motor controller of the system and controlling the pullback motor using a pullback motor controller of the system; (iv) controlling, or sending commands to, via a control processor of the system, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns; (v) conditioning or controlling, via a synchronization processor of the one or more processors, first and second encoder signals, wherein the system further includes the first encoder signal that operates to be available to the rotary motor controller and the second encoder signal that operates to be available to the pullback motor controller; and/or (vi) conditioning or controlling, via a synchronization processor of the one or more processors, first and second encoder signals before the synchronization processor interfaces with the data acquisition processor such that each time a depth scan is acquired on the imaging data input, information from the first and second encoder signals is recorded for each of the rotary motor and the pullback motor to record an exact or approximate beam position for the depth scan, wherein the system further includes the first encoder signal that operates to be available to the rotary motor controller and the second encoder signal that operates to be available to the pullback motor controller.

In one or more method embodiments, the one or more processors further include a data acquisition processor operating to acquire the imaging data obtained by the imaging apparatus or system; and the one or more processors include a synchronization processor, and the system further includes a first encoder signal that operates to be available to the rotary motor controller and a second encoder signal that operates to be available to the pullback motor controller, wherein the synchronization processor operates to condition or control the first and second encoder signals before the synchronization processor interfaces with the data acquisition processor such that each time a depth scan is acquired on the imaging data input, information from the encoder signals is recorded for each of the rotary motor and the pullback motor to record an exact or approximate beam position for the depth scan, and the synchronization processor operates to use a single synchronization signal for the data acquisition processor to capture a position of the catheter or probe for each measured depth scan profile, wherein the method may include one or more of the following: (i) triggering, via a trigger signal of the system, a single acquisition of a depth scan and recording a value of a rotation digital counter and a pullback digital counter derived from a demodulated encoded synchronization signal that is demodulated with a demodulator of the system and/or of the data acquisition processor of the system; (ii) triggering, via a trigger signal of the system, a single acquisition of a depth scan on an analog-to-digital converter (ADC) and recording a rotation digital counter and a pullback digital counter derived from a demodulated encoded synchronization signal that is demodulated with a demodulator of the system and/or of the data acquisition processor of the system; (iii) triggering, via the trigger signal being an A-line trigger signal, a sampling of the imaging data, or triggering, via the trigger signal being a k-clock trigger signal, a sampling of the imaging data so as to uniformly acquiring the imaging data in k space; (iv) using the synchronization signal that includes or comprises resultant pulse trains which are a result or are resultant of superimposition of pulse trains from each of the first and second encoder signals that operate to switch at a defined rate per revolution of the rotary motor and/or the pullback motor, and counting, via a rotation digital counter and a pullback digital counter of the data acquisition processor, the switches such that current positions of the rotary motor and the pullback motor are measured; (v) using the encoder signal pulses have a 2 volt (V) amplitude for the rotary motor encoder signal and a 3V amplitude for the pullback motor encoder signal, wherein the rotational digital counter operates to be incremented at one or more of the following transitions: at a transition from 0V to 2V, at a transition from 3V to 5V, and/or at a transition from 0V to 5V, and the pullback digital counter operates to be incremented at one or more of the following transitions: at a transition from 0V to 3V, at a transition from 2V to 5V, and/or at a transition from 0V to 5V; and/or (vi) using the data acquisition processor having the ADC, the demodulator, and the rotation digital counter and the pullback digital counter included in the data acquisition processor.

In one or more methods, the one or more processors further include a data acquisition processor operating to acquire the imaging data obtained by the imaging apparatus or system; and the one or more processors include a synchronization processor, and the system further includes a first encoder signal that operates to be available to the rotary motor controller and a second encoder signal that operates to be available to the pullback motor controller, wherein the synchronization processor operates to condition or control the first and second encoder signals before the synchronization processor interfaces with the data acquisition processor such that each time a depth scan is acquired on the imaging data input, information from the encoder signals is recorded for each of the rotary motor and the pullback motor to record an exact or approximate beam position for the depth scan, and the synchronization processor operates to use a single synchronization signal for the data acquisition processor to capture a position of the catheter or probe for each measured depth scan profile, wherein the method(s) may further include one or more of the following: (i) triggering, via a trigger signal, a single acquisition of a depth scan and recording a value of a rotation digital counter and a pullback digital counter derived from a demodulated encoded synchronization signal that is demodulated with a demodulator of the system and/or of the data acquisition processor of the system; (ii) triggering, via a trigger signal, a single acquisition of a depth scan on an analog-to-digital converter (ADC) and recording a rotation digital counter and a pullback digital counter derived from a demodulated encoded synchronization signal that is demodulated with a demodulator of the system and/or of the data acquisition processor of the system; (iii) triggering, via the trigger signal being an A-line trigger signal, a sampling of the imaging data, or triggering, via the trigger signal being a k-clock trigger signal, a sampling of the imaging data so as to uniformly acquiring the imaging data in k space; and/or (iv) using the synchronization signal including or comprising resultant pulse trains which are pulse trains coming from the synchronization processor, wherein the synchronization processor operates to send a pulse corresponding to an index of the first encoder signal which occurs per rotation of the rotary motor except the synchronization processor modifies the pulse at a predetermined or set portion of the pullback, the predetermined or set portion of the pullback being one or more of the following: a start of the pullback where the synchronization processor modifies the pulses in such a way that the synchronization processor blanks or skips one pulse at the start of the pullback, an end of the pullback where the synchronization processor modifies the pulses in such a way that the synchronization processor blanks or skips one pulse at an end of the pullback, a start and an end of the pullback where the synchronization processor modifies the pulses in such a way that the synchronization processor blanks or skips one pulse at the start of the pullback and then another pulse at the end of the pullback, a start and/or an end of the pullback where the synchronization processor modifies the pulse in such a way that the synchronization processor introduces extra pulses and/or delays at the start of the pullback and/or at the end of the pullback, at an end of the pullback where the synchronization processor modifies the pulse to increment a frame counter of the data acquisition processor at a slower rate as the rotary motor is decelerating, and/or at a start of the pullback where the synchronization processor modifies the pulse to increment a frame counter of the data acquisition processor towards a steady rate as the rotary motor accelerates to a steady state target.

One or more method embodiments may involve or have one or more of the following conditions: (i) the data acquisition processor includes a frame counter that is incremented at a fixed, stable, or predetermined or set rate, except at a start of a pullback where the frame counter increments at about half of the predetermined or set rate or at a portion of the predetermined or set rate such that a jump between the start of the pullback and a time when the frame counter is incremented at the fixed, stable, or predetermined or set rate signals or indicates the start and/or the end of the pullback accurately and deduces an approximate or accurate recording of an exact beam position for each depth scan in a case where total pullback length and/or time is known or set; (ii) the one or more processors include a control processor that operates to control, or send commands to, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns, and the data acquisition processor includes a frame counter that is incremented at a fixed, stable, or predetermined or set rate, except, in a case where at an end of the pullback where the synchronization processor modifies the pulse to increment at a slower rate as the rotary motor is decelerating, the first encoder signal pulse trains are delayed further and the frame counter is incremented at an ever increasing number of A-line triggers, the rotary motor deceleration being controlled by the control processor or the one or more processors to coincide with the end of the pullback accurately to reduce or remove uncertainty between the end of the pullback and the start of the rotary motor deceleration and to determine the end of the pullback accurately and deduce the approximate or accurate recording of the exact beam position for each depth scan for a predetermined or set total pullback length and/or time; (iii) the rotary motor has a sharp deceleration profile and the rotary motor operates to decelerate significantly or substantially in one rotation for the number of A-line triggers occurring before the frame counter is incremented such that the deceleration profile of the rotary motor is large enough to be detected as the rotary motor slowing down rather than be detected as a variation in rotary motor rotation speed; and/or (iv) a variation in rotary motor speed operates to lead in normal operation to a pulse train every predetermined or set number of A-line triggers and the rotary motor deceleration during the time equivalent of one steady state rotation operates to be a number of A-line triggers that is larger than the predetermined or set number of A-line triggers such that a threshold value operates to be set or selected above A-line triggers and a threshold value operates to be set or selected below A-line triggers to detect the end of the pullback.

In one or more embodiments, the method(s) may further include one or more of the following: (i) determining, via a pullback status processor of the one or more processors, a pullback status indicating or detecting the start and/or the end of the pullback; (ii) initiating the deceleration of the rotary motor by the rotary motor controller and/or by the rotary motor controller and a driver, wherein the rotary motor controller and/or the driver operate to receive a command to control deceleration from the pullback status processor; (iii) receiving, via the pullback status processor, information from the rotary motor controller and/or the driver to determine the pullback status; and/or (iv) using the pullback status processor while the pullback status processor is disposed or is included in the scanning mechanism of the system.

In one or more embodiments, one or more of the following may occur: (i) the rotary motor is rotated at a velocity that is lower than a target steady state value, and then accelerated at or about the same time as the pullback motor is accelerated; (ii) the data acquisition processor includes a frame counter that is incremented at a fixed, stable, or predetermined or set rate once or as the rotary motor accelerates to the target steady state value; (iii) the one or more processors include a control processor that operates to control, or send commands to, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns, and the rotary motor acceleration is controlled by the control processor or the one or more processors to coincide with the start of the pullback accurately to reduce or remove uncertainty between the start of the pullback and the start of the rotary motor acceleration and to determine the start of the pullback accurately and deduce the approximate or accurate recording of the exact beam position for each depth scan for a predetermined or set total pullback length and/or time; (iv) the rotary motor has a sharp acceleration profile and the rotary motor operates to accelerate significantly or substantially in one rotation for the number of A-line triggers occurring before the frame counter is incremented such that the acceleration profile of the rotary motor is large enough to be detected as the rotary motor speeding up to the target steady state value rather than be detected as a variation in rotary motor rotation speed; and/or (v) a variation in rotary motor speed pre-pullback operates to lead to a pulse train every predetermined or set number of A-line triggers and the rotary motor acceleration during the time equivalent of one steady state rotation operates to be a number of A-line triggers that is larger than the predetermined or set number of A-line triggers such that a threshold value operates to be set or selected to detect the start of the pullback.

One or more method embodiments may further include one or more of the following: (i) determining, via a pullback status processor of the one or more processors, a pullback status indicating or detecting the start and/or the end of the pullback; (ii) initiating the acceleration of the rotary motor by the rotary motor controller and/or by the rotary motor controller and a driver, wherein the rotary motor controller and/or the driver operate to receive a command for controlling the acceleration from the pullback status processor; (iii) receiving, via the pullback status processor, information from the rotary motor controller and/or the driver to determine the pullback status; and/or (iv) using the pullback status processor while the pullback status processor is disposed or is included in the scanning mechanism of the system.

In one or more embodiments, a computer-readable storage medium may store at least one program that operates to cause one or more processors to execute a method for performing image synchronization for one or more imaging modalities of a system, the method comprising: using one or more imaging modalities to obtain imaging data using an imaging apparatus or system of the system; performing beam scanning, via a scanning mechanism of the system, of a catheter or probe of the system to obtain a beam position of the catheter or probe; and achieving image synchronization, via one or more processors of the system, by recording the beam position simultaneously or contemporaneously with the imaging data and enabling accurate spatial registration of the imaging data.

One or more embodiments of the present disclosure determine image synchronization.

In one or more embodiments, intraluminal imaging may be used to acquire high-resolution cross-sectional images of tissues or materials, and to enable real time visualization.

Accordingly, it is at least one broad object of the present disclosure to provide one or more optical apparatuses, systems, methods (for using and/or manufacturing) and storage mediums, such as, but not limited to, fiber optic catheters, endoscopes and/or optical coherence tomography (OCT) and/or NIRF and/or NIRAF (and/or any other imaging modality or modalities) apparatuses and systems, and methods and storage mediums, for use with same, to achieve consistent, reliable image synchronization, including at a high efficiency, and at a reasonable cost of manufacture and maintenance.

In one or more embodiments, an A-line signal may be processed in one or more ways, such as those ways, methods, techniques, etc. discussed in U.S. Pat. App. No. 62/944,064, filed on Dec. 5, 2019, the disclosure of which is incorporated by reference herein in its entirety. For example, one or more of the A-line signals may be smoothed by a 2D Gaussian filter for more reliable and accurate peak detection. Preferably, in one or more embodiments, special care or step(s) may be taken to avoid any phase delay introduced by any filtering so that the pulse location is not shifted. After such filtering, a much smoother A-line signal may be obtained. By way of at least another example, in one or more method embodiments, additional filtering (e.g., 1D filtering) may be performed to smooth A-lines. The pulse in the one-dimensional signal may correspond to a vessel wall. The rising edge of the pulse may be where the edge pixel of the A-line lies. By detecting the edge pixel in each A-line, the two-dimensional edge detection issue may be converted into a simpler one-dimensional pulse detection issue. In other words, one or more embodiments of the present disclosure may simplify at least one lumen edge, stent, and/or artifacts detection approach and provide a solution at the same time.

In one or more embodiments, an additional step of finding and calculating the peaks and width parameters for lumen edge, stent(s) and/or artifact(s) may be performed, for example, as discussed in U.S. Pat. App. No. 62/944,064, filed on Dec. 5, 2019, the disclosure of which is incorporated by reference herein in its entirety. In one or more embodiments, the peak or threshold (or other measurements/calculations) information may be applied to detecting and guiding one or more optical connections. In one or more embodiments, for each A-line signal, the highest peak may be detected within the proper FOV range. In at least one embodiment, there may be three (3) types of widths defined for the detected peak. The first may be a half-max width that may be detected using an adaptive threshold based on mean and maximum values of the smoothed A-line. By way of at least one embodiment example, the threshold may be computed, as follows:

$$Threshold=(mean+peak)/2,$$

where "mean" is the average of the smoothed A-line and "peak" is the maximum value of the smoothed A-line. This threshold may be used to detect the most significant pulse corresponding to the lumen edge in a specific A-line. Any pulse above the threshold may be an edge pulse candidate in one or more embodiments. The largest pulse among all the candidates in terms of area under the pulse may be considered to be the maximum peak (or the "most significant pulse"). The second width of the highest peak may be defined as the one dimensional gradient signal along the A-line in the vicinity of the maximum peak, and may be used to identify the exact location of the lumen edge point in the smoothed A-line. The third width of the same peak may be defined along the A-line similar to the second width. However, for the third width, the gradient value will drop from its peak value to zero, which indicates the point that the value change stops and begins reversing its direction. By placing together all the lumen edge points thus detected from all the A-lines in one or more embodiments, the lumen edge for the vessel may be formed as a function of maximum peak locations vs. A-line indices.

As a further example, another approach to find the threshold is to find the average between the max peak and min peak as:

$$Threshold=(min+peak)/2.$$

A further alternative approach is to find the threshold based on the max peak as:

$$Threshold=(peak)\times 2/3.$$

The location of the highest peak of the one dimensional gradient signal along the A-line in the vicinity of the maximum peak may be used to identify the exact location of the lumen edge point in the smoothed A-line. Again, in one or more embodiments, the lumen edge data may contain or include artifact edge pixels.

In one or more embodiments, stent, peak, and/or edge detection may be performed and/or a guide wire artifact may be determined/detected and removed as discussed in U.S. Pat. App. No. 62/944,064, filed on Dec. 5, 2019, the disclosure of which is incorporated by reference herein in its entirety. In one or more embodiments, the lumen edge may be output and/or the stent strut center location (and/or other stent strut location information) may be output as discussed, for example, in U.S. Pat. App. No. 62/944,064, filed on Dec. 5, 2019, the disclosure of which is incorporated by reference herein in its entirety. A 1D smoothing filter may be applied to or used on the lumen edge results. The lumen edge and/or stent strut center location information (and/or other stent strut location information) may be output to a desired format, may be stored in a memory, may be printed, may be displayed on a display, etc.

As discussed in U.S. Pat. App. No. 62/944,064, filed on Dec. 5, 2019, the disclosure of which is incorporated by reference herein in its entirety, the OCT image in polar coordinates (e.g., of a stented vessel) may be displayed vertically (rather than, or in addition to, horizontally), and/or may be displayed with a corresponding OCT image in Cartesian Coordinates using at least one apparatus or system for performing lumen, stent, and/or artifacts detection techniques in accordance with one or more aspects of the present disclosure.

In accordance with at least one aspect of the present disclosure and as aforementioned, one or more additional methods for lumen, stent, and/or artifacts detection of OCT images are provided herein, or may be used with one or more of the features or aspects of the present disclosure, and are discussed in U.S. patent application Ser. No. 16/414,222, filed on May 16, 2019, the entire disclosure of which is incorporated by reference herein in its entirety.

In one or more embodiments, one may use either the pulse width or the area under the 1D signal pulse as the measure of the signal pulse size as discussed in U.S. patent application Ser. No. 16/414,222, filed on May 16, 2019, the entire disclosure of which is incorporated by reference herein in its entirety.

Using the noticeable differences of the falling raising gradient ratio and the differences in a size of the A-line pulses, the artifact region locations corresponding to the guidewire and stent struts in the detected lumen edge may be identified using simple thresholding where the threshold may be set, for example, as:

PulseSizeThreshold=mean−sigma×$k1$

Or

FRGRThreshold=mean+sigma×$k2$, where "mean" and "sigma" are the mean and standard deviation of the corresponding signal, and k1, k2 are empirical parameters preferably chosen, but not limited to, between 1 to 2.

An alternative approach to calculate the thresholds may be:

PulseSizeThreshold=mean+(peak−mean)/3

Or

FRGRThreshold=mean+(peak−mean)/3

Furthermore, as another alternative, the thresholds may also be calculated as:

PulseSizeThreshold=peak−(peak−mean)/2

Or

FRGRThreshold=peak−(peak−mean)/2

Preferably, in one or more embodiments, these identified edge points are not considered as the lumen edge and are not used for lumen parameter calculation.

One advantage of using one dimensional A-line signal processing for lumen edge detection is that there may be a multi-peak pattern of these boundary regions from the A-line signal because both stents and lumen edge peaks exist in the A-line signal. For example, as discussed in U.S. patent application Ser. No. 16/414,222, filed on May 16, 2019, the entire disclosure of which is incorporated by reference herein in its entirety, the boundary region may produce clustered multi-peak pulses in the A-line signal. Multi-peak pulses may be detected using the same threshold used in the maximum peak detection step as discussed above, and is not repeated herein as a result. If a falling edge of a peak rises again before the falling edge falls below the threshold, a multi-peak pulse is considered to be identified in at least one embodiment. Preferably, if a pulse is detected as a multi-peak pulse, the lumen edge data from that A-line may be considered as the boundary region of the stent struts and guidewire and removed from lumen edge detection. In one or more embodiments, multi-peaks not in the boundary region may be retained, and are preferably retained in one or more embodiments.

Even if a falling edge of a peak falls below the threshold and then raises again to form another peak, it may still be considered as a multi-peak pulse. The correct identification of the lumen edge may then rely on the major peak detection and the size of the front peak in at least one embodiment. If the front peak is identified as the artifacts, such as, but not limited to, a stent or guidewire, the second peak may be the lumen edge. There may be small vessel branch presented in the tissue underneath the vessel wall, which may end up manifesting as two separate peaks in a single A-line in a similar manner in one or more embodiments. In such a case, the front peak without the narrow width may be the lumen edge. At least one way to distinguish multi-peak pulses between the valid lumen edge versus an influence of one or more artifacts is determining whether they are located within the boundary regions. Therefore, the mutli-peak cases may be further classified into the non-boundary region and boundary region cases, and they may be removed from the detected lumen edge only in the boundary regions.

By way of another example and alternative to the aforementioned example, horizontal gradients may be used to identify and remove the lumen edge data corresponding to the boundary region between the soft tissue and narrow artifacts. As discussed in U.S. patent application Ser. No. 16/414,222, filed on May 16, 2019, the entire disclosure of which is incorporated by reference herein in its entirety, a gradient across the A-lines may display a pattern of many shadows (which may include one or more artifact shadows) caused by the light blocking artifacts.

For each detected lumen edge point, the average values of across the A-lines gradient below the edge point may be computed as discussed in U.S. patent application Ser. No. 16/414,222, filed on May 16, 2019, the entire disclosure of which is incorporated by reference herein in its entirety. These average values reflect the locations of the shadows caused by the light blocking artifacts. Given the directional property of the gradient across the A-lines, the bright to dark edge produces a rising peak while the dark to bright edge produces a falling peak. For each dark shadow produced by the stent strut, the shadow is bordered by a rising peak at one side and by a falling edge at the other side.

A computer, such as the console or computer 1200, 1200', may perform any of the steps, processes, and/or techniques discussed herein for any apparatus and/or system being manufactured or used, including, but not limited to, apparatus or system 100, apparatus or system bow, apparatus or system 100', apparatus or system 100", apparatus or system 100'", any of the embodiments shown in FIGS. 1-7, 9-11, and 13-14, any other apparatus or system discussed herein, etc.

Figure 9:
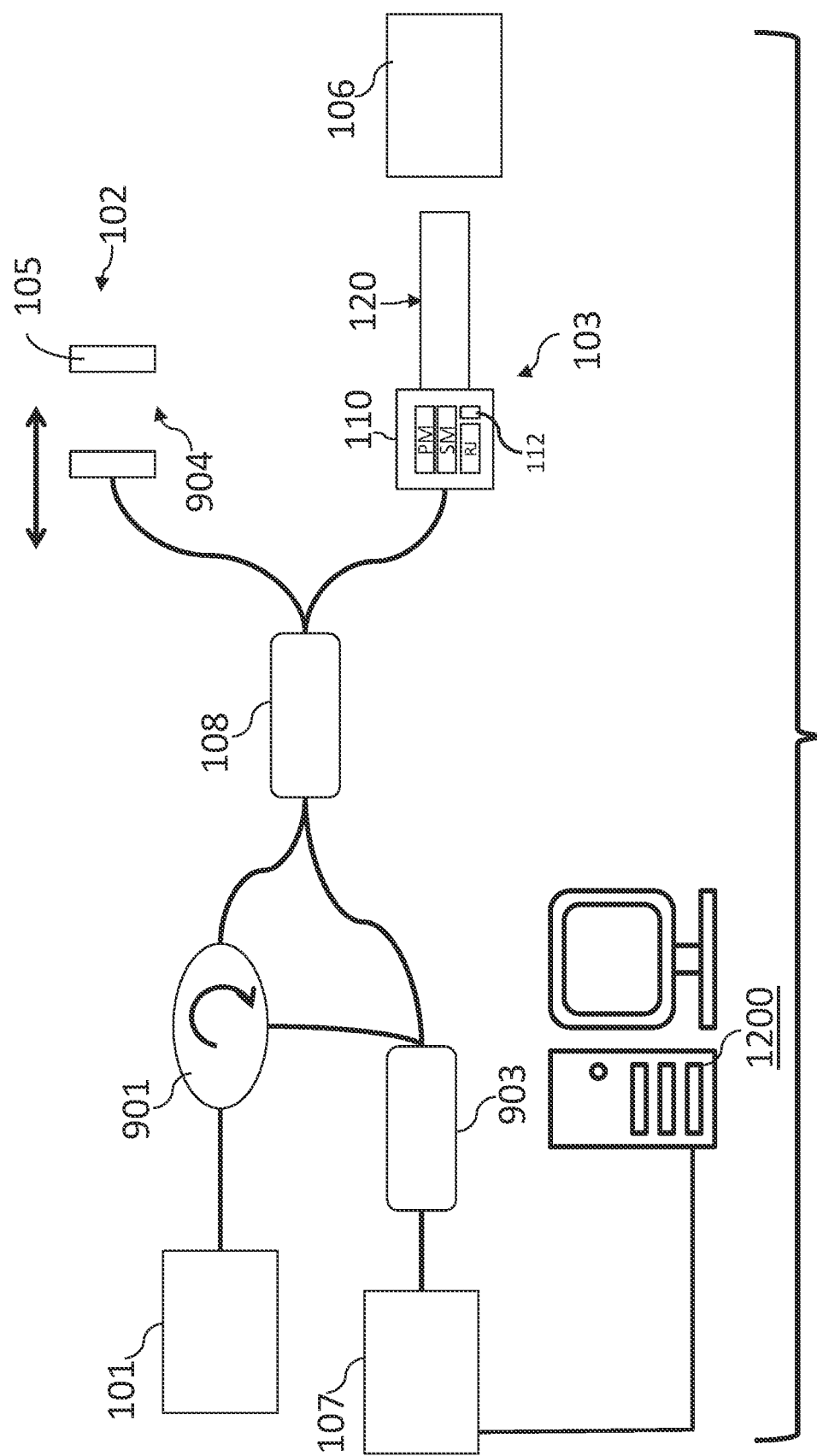
FIG. 9 is a diagram showing an embodiment of at least another system which can utilize one or more image synchronization techniques in accordance with one or more aspects of the present disclosure.

In accordance with one or more further aspects of the present disclosure, bench top systems may be utilized with the techniques, such as, but not limited to, the image synchronization techniques, disclosed herein. FIG. 9 shows an example of a system that can utilize the image synchronization techniques for a bench-top such as for ophthalmic applications. A light from a light source 101 delivers and splits into a reference arm 102 and a sample arm 103 with a deflecting (or deflection) section 108. A reference beam goes through a length adjustment section 904 (which is optional in one or more embodiments) and is reflected from a reference mirror (such as reference mirror or reference reflection 105 shown in FIG. 1) in the reference arm 102 while a sample beam is reflected or scattered from a sample, target or object 106 in the sample arm 103 (e.g., via the PIU 110 and the catheter 120). In one embodiment, both beams combine at the deflecting/deflection section 108 and generate interference patterns. In one or more embodiments, the beams go to the combiner 903, and the combiner 903 combines both beams via the circulator 901 and the deflecting section 108. The combined beams preferably are delivered to one or more detectors (such as the one or more detectors 107). The output of the beam splitter (see e.g., beam splitter 104 in FIG. 1), the deflecting section 108, and/or an interferometer is continuously acquired with one or more detectors, such as the one or more detectors 107. The electrical analog signals are converted to the digital signals to analyze them with a computer, such as, but not limited to, the computer 1200 (see FIG. 1; also shown in FIGS. 3-7, 9-11 and 13 discussed further below), the computer 1200' (see e.g., FIG. 14 discussed further below), etc.

Figure 10:
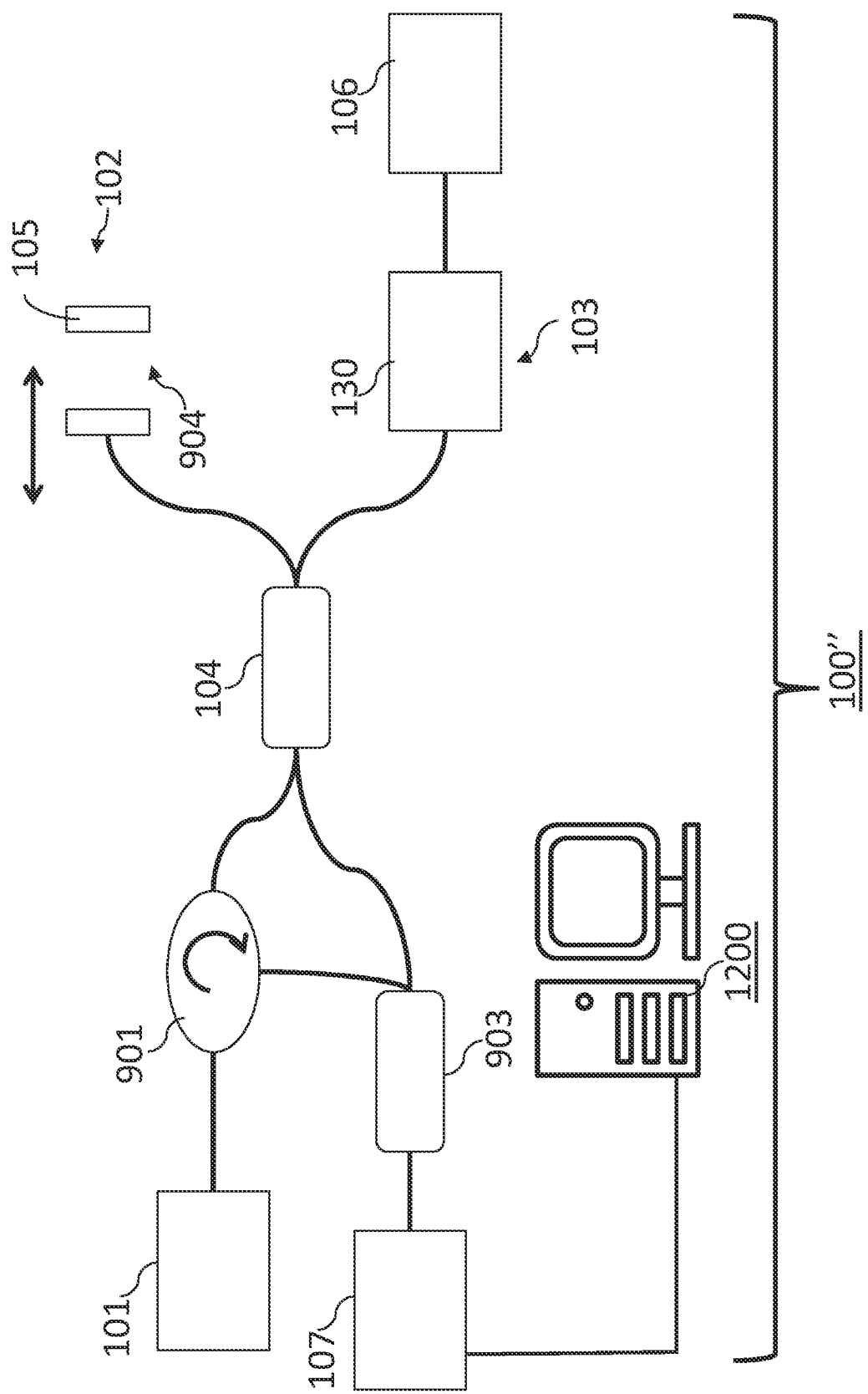
FIG. 10 is a diagram showing an embodiment of at least a further system which can utilize one or more one or more image synchronization techniques in accordance with one or more aspects of the present disclosure.

In one or more embodiments, the sample arm 103 may include a phase shift unit 130 for a bench top system(s) as shown in system 100" in FIG. 10. The sample 106 may be located at the place of the mirror 105 used with the phase shift unit 130 (e.g., as shown in FIG. 1). A light from a light source 101 delivers and splits into a reference arm 102 and a sample arm 103 with a splitter 104. A reference beam goes through a length adjustment section 904 and is reflected from a reference mirror (such as reference mirror 105 shown in FIGS. 9-11) in the reference arm 102 while a sample beam is reflected or scattered from a sample, target and/or object 106 through a phase shift unit (such as the phase shift unit 130) in the sample arm 103. In one embodiment, both beams combine at the splitter 104 and generate interference patterns. In one or more embodiments, the beams go to the combiner 903, and the combiner 903 combines both beams via the circulator 901 and the splitter 104, and the combined beams are delivered to one or more detectors (such as the one or more detectors 107). The output of the beam splitter 104 and/or an interferometer is continuously acquired with one or more detectors, such as the one or more detectors 107. The electrical analog signals are converted to the digital signals to analyze them with a computer.

There are many ways to compute rotation, intensity, or any other measurement discussed herein, and/or to control and/or manufacture an MMOCT device/apparatus, system and/or storage medium, digital as well as analog. In at least one embodiment, a computer, such as the console or computer 1200, 1200', may be dedicated to control and/or use OCT devices, systems, methods and/or storage mediums for use therewith described herein. One or more other imaging modalities (e.g., NIRF, NIRAF, IVUS, etc.) may be used with one or more embodiments.

Figure 11:
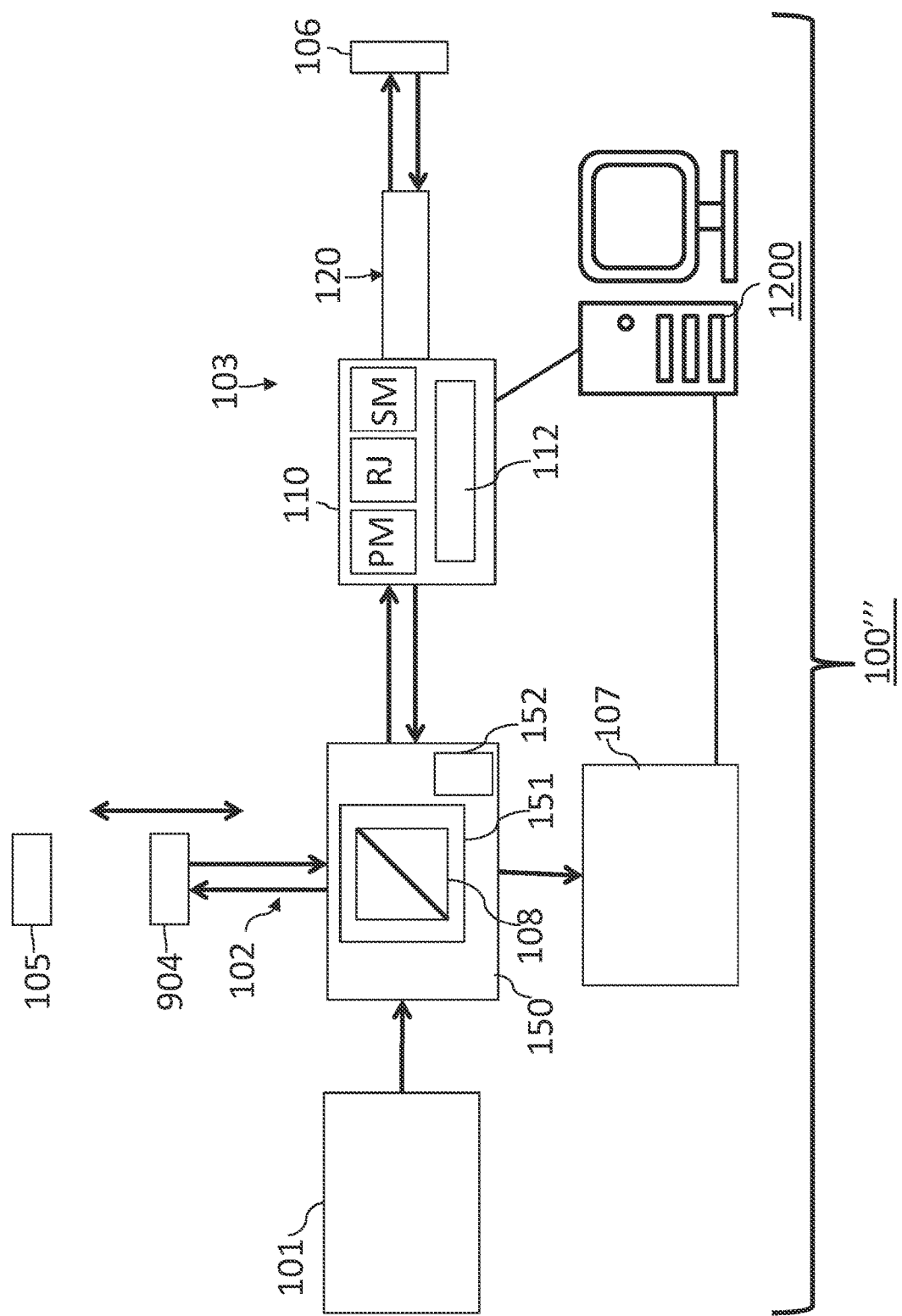
FIG. 11 is a diagram showing an embodiment of at least yet a further system which can utilize one or more one or more image synchronization techniques in accordance with one or more aspects of the present disclosure.

In accordance with one or more further aspects of the present disclosure, one or more other systems may be utilized with the image synchronization techniques disclosed herein. FIG. 11 shows an example of a system 100''' that may utilize the image synchronization techniques such as for ophthalmic applications. A light from a light source 101 delivers and splits into a reference arm 102 and a sample arm 103 with a deflecting section 108 (e.g., a beam splitter or other deflecting or deflected section discussed herein) located inside of an OCT imaging engine 150, which may also include an OCT interferometer 151 (which may house or include the deflecting section 108) and a swept source engine 152 in one or more embodiments. A reference beam may pass through a length adjustment section 904, which may operate to change the distance of a reference mirror (such as reference mirror or reference reflection 105; also shown in FIG. 1) and is reflected from the reference reflection 105 in the reference arm 102 while a sample beam is reflected or scattered from a sample, target or object 106 in the sample arm 103. In one embodiment, both beams combine at the deflecting section 108 and generate interference patterns. In one or more embodiments, the combined beams are delivered to one or more detectors. The output of the interferometer 151 is continuously acquired with one or more detectors, such as the one or more detectors 107. The electrical analog signals are converted to the digital signals to analyze them with a computer, such as, but not limited to, the computer 1200 (see e.g., FIG. 1; also shown in FIGS. 3-7, 9-11 and 13 discussed further below), the computer 1200' (see e.g., FIG. 14 discussed further below), etc. In one or more embodiments, the sample arm 103 includes the PIU 110 and the catheter 120 so that the sample beam is reflected or scattered from the sample, target or object 106 as discussed herein. In one or more embodiments, the PIU 110 may include one or more motors to control the pullback operation of the catheter 120 (or one or more components thereof) and/or to control the rotation or spin of the catheter 120 (or one or more components thereof). For example, the PIU 110 may include a pullback motor (PM) and a spin motor (SM), and/or may include a motion control unit 112 that operates to perform the pullback and/or rotation features using the pullback motor PM and/or the spin motor SM. Additionally or alternatively, a pullback motor (e.g., the pullback motor 270, 570) and/or a rotary motor (e.g., the rotary motor 260, 560) as discussed above may be used. As discussed herein, the PIU 110 may include a rotary junction (e.g., rotary junction RJ as shown in FIGS. 9 and 11). The rotary junction RJ may be connected to the spin motor SM so that the catheter 120 may obtain one or more views or images of the sample 106. The computer 1200 (or the computer 1200') may be used to control one or more of the pullback motor PM, the spin motor SM and/or the motion control unit 112. An OCT system may include one or more of the OCT engine 150, a computer (e.g., the computer 1200, the computer 1200', etc.), the PIU 110, the catheter 120, a monitor, etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

Unless otherwise discussed herein, like numerals indicate like elements. For example, while variations or differences exist between the systems/apparatuses, such as, but not limited to, the system 100, the system bow, the system 100', the system 100", the system 100''', the systems/apparatuses of FIGS. 1-7, etc. (e.g., differences between the position(s) of the reference reflection 105 (and/or reference arm 102) depending on the OCT system or method being used), one or more features thereof may be the same or similar to each other, such as, but not limited to, the light source 101, the deflecting section 108 or other component(s) thereof (e.g., the console 1200, the console 1200', etc.). Those skilled in the art will appreciate that the light source 101, the at least one detector 107 and/or one or more other elements of the system 100, may operate in the same or similar fashion to those like-numbered elements of one or more other systems, such as, but not limited to, the system bow, the system 100', the system 100", the system 100'", etc. as discussed herein. Those skilled in the art will appreciate that alternative embodiments of the system 100, the system bow, the system 100', the system 100", the system 100'", the systems/apparatuses of FIGS. 1-7, and/or one or more like-numbered elements of one of such systems, while having other variations as discussed herein, may operate in the same or similar fashion to the like-numbered elements of any of the other systems (or component(s) thereof) discussed herein. Indeed, while certain differences exist between the system 100, the system bow, the system 100', the system 100" and the system 100'", the systems/apparatuses of FIGS. 1-7, etc. as discussed herein, there are similarities between the apparatuses/systems discussed herein. Likewise, while the console or computer 1200 may be used in one or more systems (e.g., the system 100, the system 100a, the system 100', the system 100", the system 100'", the systems/apparatuses of FIGS. 1-7, etc.), one or more other consoles or computers, such as the console or computer 1200', may be used additionally or alternatively.

Figure 12:
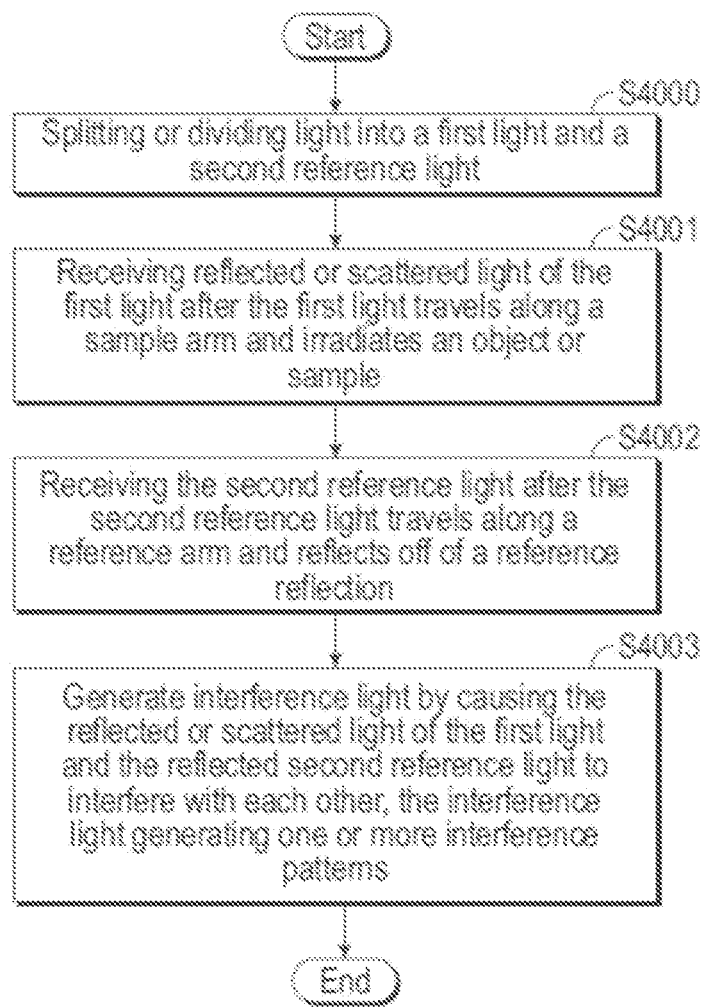
FIG. 12 is a flow diagram illustrating at least one method embodiment of performing an imaging feature, function, or technique that may be used with one or more one or more image synchronization techniques in accordance with one or more aspects of the present disclosure.

In accordance with one or more aspects of the present disclosure, one or more methods for image synchronization are provided herein, and one or more methods for performing imaging are provided herein. FIG. 12 illustrates a flow chart of at least one embodiment of a method for performing imaging. Preferably, the method(s) may include one or more of the following: (i) splitting or dividing light into a first light and a second reference light (see step S4000 in FIG. 12); (ii) receiving reflected or scattered light of the first light after the first light travels along a sample arm and irradiates an object or a sample (see step S4001 in FIG. 12); (iii) receiving the second reference light after the second reference light travels along a reference arm and reflects off of a reference reflection (see step S4002 in FIG. 12); and (iv) generating interference light by causing the reflected or scattered light of the first light and the reflected second reference light to interfere with each other (for example, by combining or recombining and then interfering, by interfering, etc.), the interference light generating one or more interference patterns (see step S4003 in FIG. 12). One or more methods may further include using low frequency monitors to update or control high frequency content to improve image quality. For example, one or more embodiments may use balanced detection, polarization diversity, automated polarization control, etc. and/or image synchronization to achieve improved image quality. In one or more embodiments, an imaging probe may be connected to one or more systems (e.g., the system 100, the system bow, the system 100', the system 100", the devices, apparatuses or systems of FIGS. 1-7, any other system or apparatus discussed herein, etc.) with a connection member or interface module. For example, when the connection member or interface module is a rotary junction for an imaging probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the imaging probe may be separate from the detection portion of the imaging probe. For example, in one or more applications, a probe may refer to the illumination assembly, which includes an illumination fiber (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: a detection fiber, a detector (e.g., the one or more detectors 107, a spectrometer, etc.), the computer 1200, the computer 1200', etc. The detection fibers may surround the illumination fiber, and the detection fibers may or may not be covered by a grating, a spacer, a lens, an end of a probe or catheter, etc.

There are many ways to compute power and/or detect lumen edge(s) and artifact(s), and/or detect and/or guide optical connections/disconnections, digital as well as analog. In at least one embodiment, a computer, such as the console or computer 1200, 1200', may be dedicated to the control and the monitoring of the OCT devices, systems, methods and/or storage mediums described herein.

The electric signals used for imaging may be sent to one or more processors, such as, but not limited to, a computer 1200 (see e.g., FIGS. 1-7, 9-11, and 13), a computer 1200' (see e.g., FIG. 14), etc. as discussed further below, via cable(s) or wire(s), such as, but not limited to, the cable(s) or wire(s) 113 (see FIG. 13).

Figure 13:
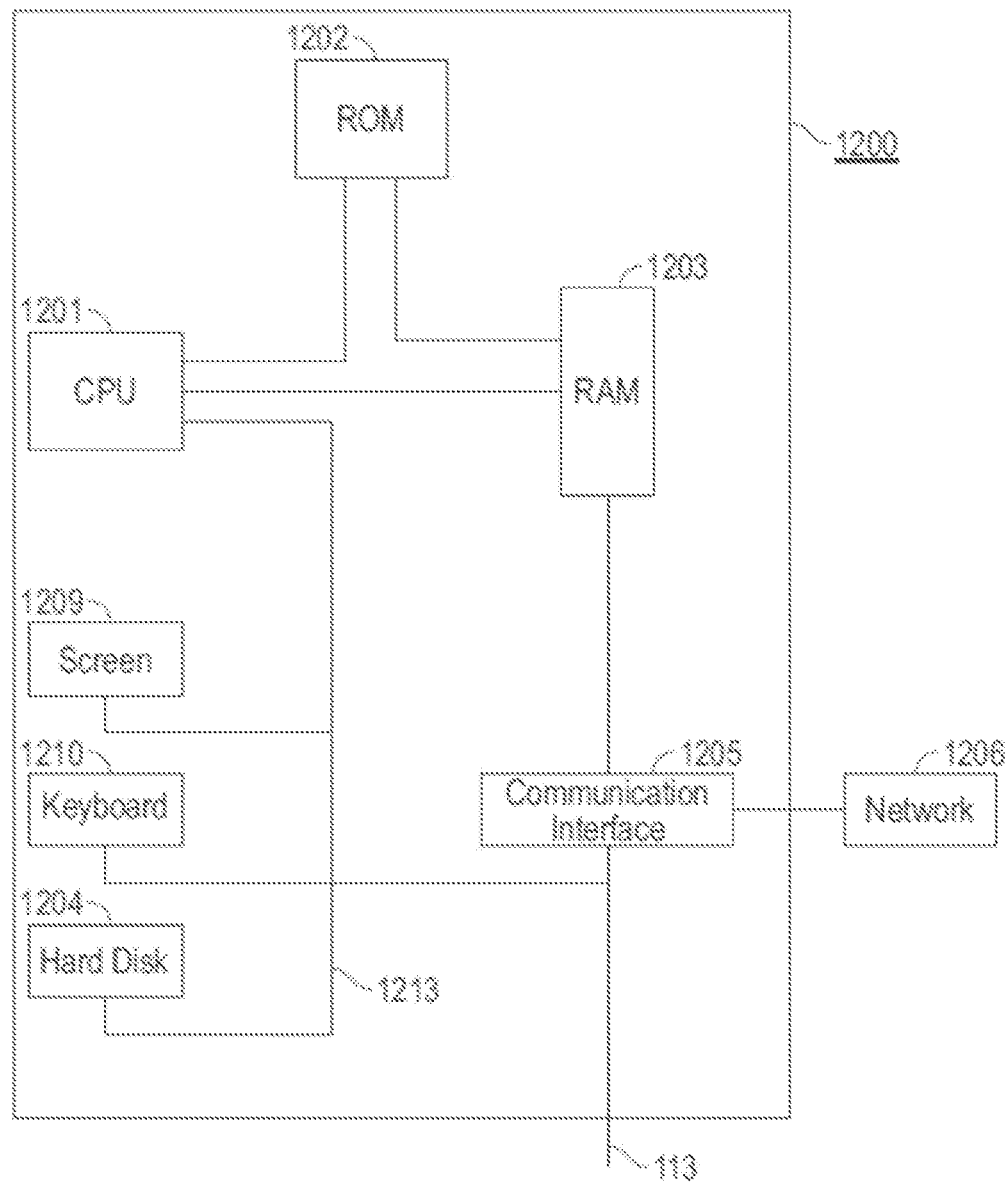
FIG. 13 shows a schematic diagram of an embodiment of a computer that may be used with one or more embodiments of at least one apparatus, system, method, and/or storage medium, including, but not limited to, for performing one or more one or more image synchronization techniques, in accordance with one or more aspects of the present disclosure.

Various components of a computer system 1200 (see e.g., the console or computer 1200 as shown in FIGS. 1-7 and 9-11) are provided in FIG. 13. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 13). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a FORJ or a device or system using same, such as, but not limited to, the system 100, the system bow, the system 100', the system 100", the system 100'", and/or the systems/apparatuses of FIGS. 1-7, discussed herein above, via one or more lines 1213), and one or more other computer systems 1200 may include one or more combinations of the other aforementioned components. The CPU 1201 is configured to read and perform computer-executable instructions stored in a storage medium. The computer-executable instructions may include those for the performance of the methods and/or calculations described herein. The computer system 1200 may include one or more additional processors in addition to CPU 1201, and such processors, including the CPU 1201, may be used for controlling and/or manufacturing a device, system or storage medium for use with same or for use with any lumen detection, stent(s) detection, artifact(s) detection, and/or image synchronization technique(s) discussed herein. The system 1200 may further include one or more processors connected via a network connection (e.g., via network 1206). The CPU 1201 and any additional processor being used by the system 1200 may be located in the same telecom network or in different telecom networks (e.g., performing, manufacturing, controlling and/or using technique(s) may be controlled remotely).

Figure 14:
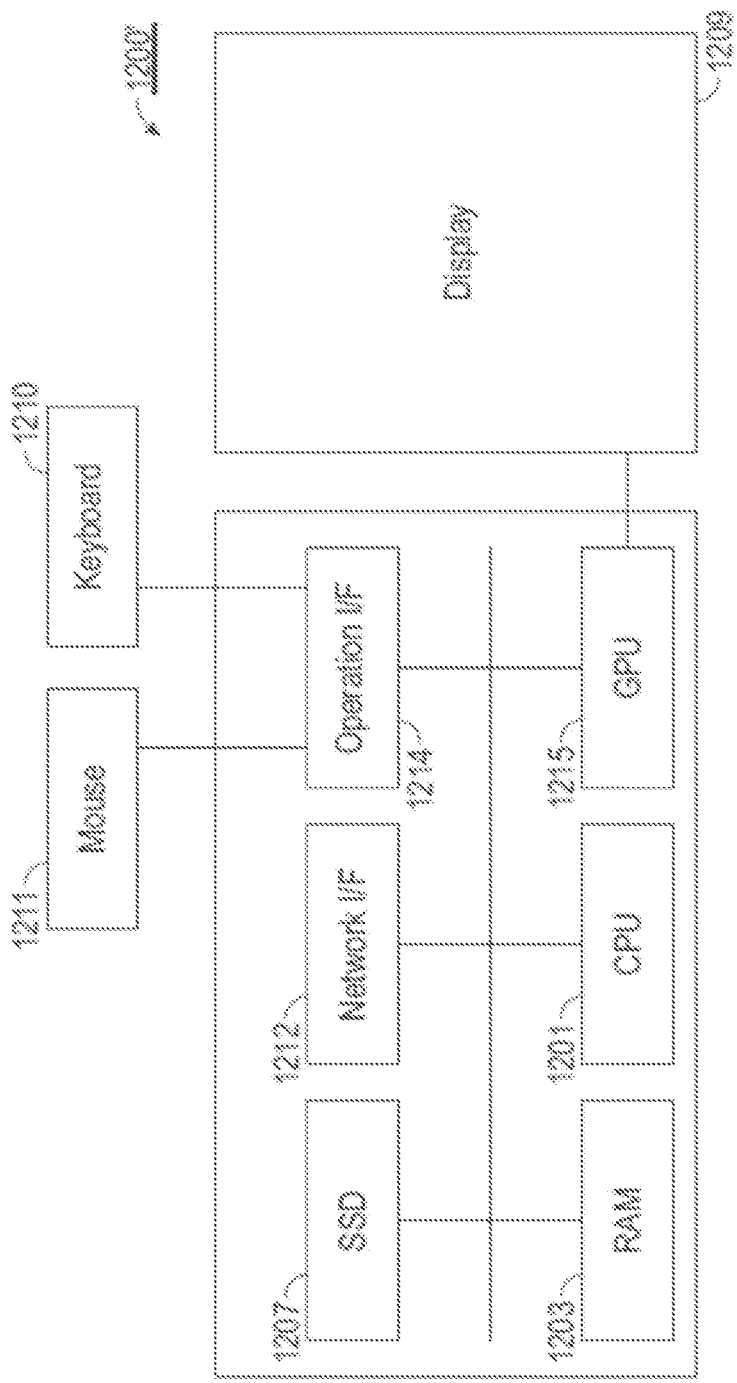
FIG. 14 shows a schematic diagram of another embodiment of a computer that may be used with one or more embodiments of at least one apparatus, system, method, and/or storage medium, including, but not limited to, for performing one or more one or more image synchronization techniques, in accordance with one or more aspects of the present disclosure.

The I/O or communication interface 1205 provides communication interfaces to input and output devices, which may include the light source 101, a RJ, a PM, an SM, unit 150, unit 112, a microphone, a communication cable and a network (either wired or wireless), a keyboard 1210, a mouse (see e.g., the mouse 1211 as shown in FIG. 14), a touch screen or screen 1209, a light pen and so on. The Monitor interface or screen 1209 provides communication interfaces thereto.

Any methods and/or data of the present disclosure, such as the methods for using and/or manufacturing a device, system or storage medium for use with same and/or method(s) for detecting lumen edge(s), stent(s), and/or artifact(s), including in OCT image(s), and/or for image synchronization, as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 14), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined, limited, or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, devices, systems, and computer-readable storage mediums related to the processors, such as, but not limited to, the processor of the aforementioned computer 1200, the processor of computer 1200', etc., as described above may be achieved utilizing suitable hardware, such as that illustrated in the figures. Functionality of one or more aspects of the present disclosure may be achieved utilizing suitable hardware, such as that illustrated in FIG. 13. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 13 or FIG. 14) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 14. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid-state drive (SSD) 1207. Preferably, the computer or console 1200' includes a display 1209. The computer 1200' may connect with a rotary junction (e.g., RJ of FIG. 9, RJ of FIG. 11, etc.), the motor PM, the motor SM, and/or one or more other components of a system (e.g., the system 100, the system bow, the system 100', the system 100", the system 100''', the systems/apparatuses of FIGS. 1-7, the systems/apparatuses of FIGS. 9-11, etc.) via the operation interface 1214 or the network interface 1212. A computer, such as the computer 1200, 1200', may include the RJ, PM and/or the SM in one or more embodiments. The operation interface 1214 is connected with an operation unit such as a mouse device 1211, a keyboard 1210 or a touch panel device. The computer 1200' may include two or more of each component. Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', etc.

A computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 1200, 1200', communicates with the PIU 110, the rotary junction (e.g., the RJ, etc.), the motor PM, the motor SM, the catheter 120 and/or one or more other components of a system, such as the system 100, bow, 100', 100", 100''', etc., to perform imaging and/or image synchronization, and reconstructs an image from the acquired intensity data. The monitor or display 1209 displays the reconstructed image, and may display other information about the imaging condition or about an object to be imaged. The monitor 1209 also provides a graphical user interface for a user to operate a system (e.g., the system 100, the system bow, the system 100', the system 100", the system 100''', etc.), for example when performing OCT or other imaging technique, including, but not limited to, detection of lumen edge(s) and/or artifact(s), and/or image synchronization. An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system bow, the system 100', the system 100", the system 100''', the systems/apparatuses of FIGS. 1-7, the systems/apparatuses of FIGS. 9-11, etc.) to set or change the imaging condition, and to start or end the imaging, and/or to start or end the lumen detection, stent(s) detection, artifact(s) detection, and/or perform image synchronization. The laser source 101 of an OCT system as aforementioned may have interfaces to communicate with the computers 1200, 1200' to send and receive the status information and the control signals.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 7,872,759; 8,289,522; and 8,928,889 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942 and U.S. Patent Publication Nos. 2010/0092389, 2012/0101374, 2016/0228097, 2018/0045501 and 2018/0003481, each of which patents, patent publications and patent application(s) are incorporated by reference herein in their entireties. As aforementioned, any feature or aspect of the present disclosure may be used with OCT imaging systems, apparatuses, methods, storage mediums or other aspects or features as discussed in U.S. patent application Ser. No. 16/414,222, filed on May 16, 2019, the entire disclosure of which is incorporated by reference herein in its entirety, and as discussed in U.S. Pat. App. No. 62/944,064, filed on Dec. 5, 2019, the disclosure of which is incorporated by reference herein in its entirety.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications, equivalent structures and functions.

The invention claimed is:

1. A system for performing image synchronization, comprising:
- an imaging apparatus using one or more imaging modalities to obtain imaging data;
- a scanning mechanism that operates to perform beam scanning of a catheter or probe of the system to obtain a beam position of the catheter or probe;
- one or more processors that operate to achieve image synchronization by recording the beam position simultaneously or contemporaneously with the imaging data and that operate to enable accurate spatial registration of the imaging data, the one or more processors further including a data acquisition processor that operates to acquire the imaging data obtained by the imaging apparatus, and the one or more processors further including a synchronization processor;
- a rotary motor that operates to rotate the scanning mechanism, a part of the scanning mechanism, and/or the catheter or probe, and a pullback motor that operates to control pullback of the catheter or probe, wherein the catheter or probe beam scanning is performed by the scanning mechanism using the rotary motor and the pullback motor;
- a rotary motor controller and a pullback motor controller, wherein the one or more processors operate to communicate with, control, or send commands to, the rotary motor controller and the pullback motor controller; and
- a first encoder signal that operates to be available to the rotary motor controller and a second encoder signal that operates to be available to the pullback motor controller,
- wherein the synchronization processor operates to condition or control the first and second encoder signals before the synchronization processor interfaces with the data acquisition processor such that each time a depth scan is acquired on the imaging data input, information from the first and second encoder signals is recorded for each of the rotary motor and the pullback motor to record an exact or approximate beam position for the depth scan, and the synchronization processor operates to use a single synchronization signal for the data acquisition processor to capture a position of the catheter or probe for each measured depth scan profile.

2. The system of claim 1, wherein the one or more processors further include a hardware management processor, operating to control the data acquisition processor.

3. The system of claim 1, wherein one or more of the following occurs or exists:
 (i) the one or more processors further include a hardware management processor operating to control the data acquisition processor; and/or
 (ii) the one or more processors include a control processor that operates to control, or send commands to, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns.

4. The system of claim 1,
wherein one or more of the following occurs or exists:
 (i) a trigger signal is used to trigger a single acquisition of a depth scan and to record a value of a rotation digital counter and a pullback digital counter derived from a demodulated encoded synchronization signal that is demodulated with a demodulator of the system and/or of the data acquisition processor of the system;
 (ii) a trigger signal is used to trigger a single acquisition of a depth scan on an analog-to-digital converter (ADC);

(iii) a trigger signal is used as an A-line trigger signal that operates to trigger a sampling of the imaging data, or the trigger signal is a k-clock trigger signal that operates to trigger a sampling of the imaging data so as to uniformly acquiring the imaging data in k space;
(iv) the synchronization signal includes or comprises resultant pulse trains which are a result or are resultant of superimposition of pulse trains from each of the first and second encoder signals that operate to switch at a defined rate per revolution of the rotary motor and/or the pullback motor, and a rotation digital counter and a pullback digital counter of the data acquisition processor operate to count the switches such that current positions of the rotary motor and the pullback motor are measured;
(v) the encoder signal pulses have a 2 volt (V) amplitude for the rotary motor encoder signal and a 3V amplitude for the pullback motor encoder signal, the rotational digital counter operates to be incremented at one or more of the following transitions: at a transition from 0V to 2V, at a transition from 3V to 5V, and/or at a transition from 0V to 5V, and the pullback digital counter operates to be incremented at one or more of the following transitions: at a transition from 0V to 3V, at a transition from 2V to 5V, and/or at a transition from 0V to 5V; and/or
(vi) an analog-to-digital converter (ADC), a demodulator, a rotation digital counter, and a pullback digital counter are included in the data acquisition processor.

5. The system of claim 1,
wherein one or more of the following occurs or exists:
(i) a trigger signal is used to trigger a single acquisition of a depth scan and to record a value of a rotation digital counter and a pullback digital counter derived from a demodulated encoded synchronization signal that is demodulated with a demodulator of the system and/or of the data acquisition processor of the system;
(ii) a trigger signal is used to trigger a single acquisition of a depth scan on an analog-to-digital converter (ADC) and to record a rotation digital counter and a pullback digital counter derived from a demodulated encoded synchronization signal that is demodulated with a demodulator of the system and/or of the data acquisition processor of the system;
(iii) the trigger signal is an A-line trigger signal that operates to trigger a sampling of the imaging data, or the trigger signal is a k-clock trigger signal that operates to trigger a sampling of the imaging data so as to uniformly acquiring the imaging data in k space;
(iv) the synchronization signal includes or comprises resultant pulse trains which are pulse trains coming from the synchronization processor, and the synchronization processor operates to send a pulse corresponding to an index of the first encoder signal which occurs per rotation of the rotary motor except the synchronization processor operates to modify the pulse at a predetermined or set portion of the pullback, the predetermined or set portion of the pullback being one or more of the following: a start of the pullback where the synchronization processor operates to modify the pulses in such a way that the synchronization processor operates to blank or skip one pulse at the start of the pullback, an end of the pullback where the synchronization processor operates to modify the pulses in such a way that the synchronization processor operates to blank or skip one pulse at an end of the pullback, a start and an end of the pullback where the synchronization processor operates to modify the pulses in such a way that the synchronization processor operates to blank or skip one pulse at the start of the pullback and then another pulse at the end of the pullback, a start and/or an end of the pullback where the synchronization processor operates to modify the pulse in such a way that the synchronization processor introduces extra pulses and/or delays at the start of the pullback and/or at the end of the pullback, at an end of the pullback where the synchronization processor operates to modify the pulse to increment a frame counter of the data acquisition processor at a slower rate as the rotary motor is decelerating, and/or at a start of the pullback where the synchronization processor operates to modify the pulse to increment a frame counter of the data acquisition processor towards a steady rate as the rotary motor accelerates to a steady state target; and/or
(v) the data acquisition processor includes a frame counter that is incremented once every set number of triggers.

6. The system of claim 5, wherein one or more of the following occurs or exists:
(i) the data acquisition processor includes a frame counter that is incremented at a fixed, stable, or predetermined or set rate, except at a start of a pullback where the frame counter increments at about half of the predetermined or set rate or at a portion of the predetermined or set rate such that a jump between the start of the pullback and a time when the frame counter is incremented at the fixed, stable, or predetermined or set rate signals or indicates the start and/or the end of the pullback accurately and deduces an approximate or accurate recording of an exact beam position for each depth scan in a case where total pullback length and/or time is known or set;
(ii) the one or more processors include a control processor that operates to control, or send commands to, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns, and the data acquisition processor includes a frame counter that is incremented at a fixed, stable, or predetermined or set rate, except, in a case where at an end of the pullback where the synchronization processor operates to modify the pulse to increment at a slower rate as the rotary motor is decelerating, the first encoder signal pulse trains are delayed further and the frame counter is incremented at an ever increasing number of A-line triggers, the rotary motor deceleration being controlled by the control processor or the one or more processors to coincide with the end of the pullback accurately to reduce or remove uncertainty between the end of the pullback and the start of the rotary motor deceleration and to determine the end of the pullback accurately and deduce the approximate or accurate recording of the exact beam position for each depth scan for a predetermined or set total pullback length and/or time;
(iii) the rotary motor has a sharp deceleration profile and the rotary motor operates to decelerate significantly or substantially in one rotation for the number of A-line triggers occurring before a frame counter of the data acquisition processor is incremented such that the deceleration profile of the rotary motor is large enough to be detected as the rotary motor slowing down rather than be detected as a variation in rotary motor rotation speed; and/or (iv) a variation in rotary motor speed operates to lead in normal operation to a pulse train every predetermined or set number of A-line triggers and the rotary motor deceleration during the time equivalent of one steady state rotation operates to be another number of A-line triggers that is larger than the predetermined or set number of A-line triggers such that a threshold value operates to be set or selected above the predetermined or set number of A-line triggers and below the another number of A-line triggers to detect the end of the pullback.

7. The system of claim 6, wherein one or more of the following occurs or exists:

(i) the one or more processors further includes a pullback status processor that operates to determine a pullback status indicating or detecting the start and/or the end of the pullback;

(ii) a deceleration of the rotary motor is initiated by the rotary motor controller and/or by the rotary motor controller and a driver, and the rotary motor controller and/or the driver operate to receive a command to control deceleration from the pullback status processor;

(iii) the pullback status processor further operates to receive information from the rotary motor controller and/or a driver to determine the pullback status; and/or (iv) the pullback status processor is disposed or is included in the scanning mechanism of the system.

8. The system of claim 5, wherein one or more of the following occurs or exists:

(i) the rotary motor is rotated at a velocity that is lower than a target steady state value, and then accelerated at or about the same time as the pullback motor is accelerated;

(ii) the data acquisition processor includes a frame counter that is incremented at a fixed, stable, or predetermined or set rate once or as the rotary motor accelerates to a target steady state value;

(iii) the one or more processors include a control processor that operates to control, or send commands to, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns, and the rotary motor acceleration is controlled by the control processor or the one or more processors to coincide with the start of the pullback accurately to reduce or remove uncertainty between the start of the pullback and the start of the rotary motor acceleration and to determine the start of the pullback accurately and deduce the approximate or accurate recording of the exact beam position for each depth scan for a predetermined or set total pullback length and/or time;

(iv) the rotary motor has a sharp acceleration profile and the rotary motor operates to accelerate significantly or substantially in one rotation for the number of A-line triggers occurring before a frame counter of the data acquisition processor is incremented such that the acceleration profile of the rotary motor is large enough to be detected as the rotary motor speeding up to a target steady state value rather than be detected as a variation in rotary motor rotation speed; and/or (v) a variation in rotary motor speed pre-pullback operates to lead to a pulse train every predetermined or set number of A-line triggers and the rotary motor acceleration during the time equivalent of one steady state rotation operates to be another number of A-line triggers that is larger than the predetermined or set number of A-line triggers such that a threshold value operates to be set or selected above the set number of A-line triggers and below the another number of A-line triggers to detect the start of the pullback.

9. The system of claim 8, wherein one or more of the following occurs or exists:

(i) the one or more processors further includes a pullback status processor that operates to determine a pullback status indicating or detecting the start and/or the end of the pullback;

(ii) the acceleration of the rotary motor is initiated by the rotary motor controller and/or by the rotary motor controller and a driver, and the rotary motor controller and/or the driver operate to receive a command for controlling the acceleration from the pullback status processor;

(iii) the pullback status processor further operates to receive information from the rotary motor controller and/or a driver to determine the pullback status; and/or (iv) the pullback status processor is disposed or is included in the scanning mechanism of the system.

10. The system of claim 1, wherein the system further comprises or is connected to one or more of the following:

a light source that operates to produce a light;

an interference optical system that operates to: (i) receive and divide the light from the light source into a first light with which an object or sample is to be irradiated and a second reference light, (ii) send the second reference light for reflection off of a reference mirror of the interference optical system, and (iii) generate interference light by causing reflected or scattered light of the first light with which the object or sample has been irradiated and the reflected second reference light to combine or recombine, and to interfere, with each other, the interference light generating one or more interference patterns; and/or one or more detectors that operate to continuously acquire the interference light and/or the one or more interference patterns such that one or more A-lines or are obtained.

11. The system of claim 1, wherein the one or more imaging modalities includes one or more of the following: Optical Coherence Tomography (OCT), single modality OCT, multi-modality OCT, swept source OCT, optical frequency domain imaging (OFDI), intravascular ultrasound (IVUS), another lumen image(s) modality, near-infrared spectroscopy, near-infrared fluorescence (NIRF), near-infrared auto-fluorescence (NIRAF), and an intravascular imaging modality.

12. A method for controlling a system for performing image synchronization, the method comprising:

using one or more imaging modalities to obtain imaging data using an imaging apparatus of the system;

performing beam scanning, via a scanning mechanism of the system using a rotary motor of the system and a pullback motor of the system, of a catheter or probe of the system to obtain a beam position of the catheter or probe, the rotary motor operating to rotate the scanning mechanism, a part of the scanning mechanism, and/or the catheter or probe, and the pullback motor operating to control pullback of the catheter or probe;

achieving image synchronization, via one or more processors of the system, by recording the beam position simultaneously or contemporaneously with the imaging data and enabling accurate spatial registration of the imaging data;

controlling, or sending commands to, via the one or more processors of the system, a rotary motor controller of the system and a pullback motor controller of the system; and conditioning or controlling, via a synchronization processor of the one or more processors, first and second encoder signals before the synchronization processor interfaces with a data acquisition processor of the one or more processors such that each time a depth scan is acquired on the imaging data input, information from the first and second encoder signals is recorded for each of the rotary motor and the pullback motor to record an exact or approximate beam position for the depth scan, and the synchronization processor operates to use a single synchronization signal for the data acquisition processor to capture a position of the catheter or probe for each measured depth scan profile, wherein the system further includes the first encoder signal that operates to be available to the rotary motor controller and the second encoder signal that operates to be available to the pullback motor controller.

13. The method of claim 12, further comprising:
controlling, via a hardware management processor of the one or more processors, the data acquisition processor, and
acquiring, via the data acquisition processor, the imaging data obtained by the imaging apparatus.

14. The method of claim 12, further comprising:
(i) rotating at least a part of the scanning mechanism, and/or the catheter or probe using the rotary motor, and
(ii) controlling a pullback of the catheter or probe using the pullback motor.

15. The method of claim 12, further comprising one or more of the following:
(i) controlling, via a hardware management processor of the one or more processors, the data acquisition processor;
(ii) acquiring, via the data acquisition processor, the imaging data obtained by the imaging apparatus; and/or
(iii) controlling, or sending commands to, via a control processor of the one or more processors of the system, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns.

16. The method of claim 12,
wherein the method further comprises one or more of the following:
(i) triggering, via a trigger signal of the system, a single acquisition of a depth scan and recording a value of a rotation digital counter and a pullback digital counter derived from a demodulated encoded synchronization signal that is demodulated with a demodulator of the system and/or of the data acquisition processor of the system;
(ii) triggering, via a trigger signal of the system, a single acquisition of a depth scan on an analog-to-digital converter (ADC) and recording a rotation digital counter and a pullback digital counter derived from a demodulated encoded synchronization signal that is demodulated with a demodulator of the system and/or of the data acquisition processor of the system;
(iii) triggering, via a trigger signal being used as an A-line trigger signal, a sampling of the imaging data, or triggering, via the trigger signal being a k-clock trigger signal, a sampling of the imaging data so as to uniformly acquiring the imaging data in k space;
(iv) using the synchronization signal that includes or comprises resultant pulse trains which are a result or are resultant of superimposition of pulse trains from each of the first and second encoder signals that operate to switch at a defined rate per revolution of the rotary motor and/or the pullback motor, and counting, via a rotation digital counter and a pullback digital counter of the data acquisition processor, the switches such that current positions of the rotary motor and the pullback motor are measured;
(v) using the encoder signal pulses having a 2 volt (V) amplitude for the rotary motor encoder signal and a 3V amplitude for the pullback motor encoder signal, wherein the rotational digital counter operates to be incremented at one or more of the following transitions: at a transition from 0V to 2V, at a transition from 3V to 5V, and/or at a transition from 0V to 5V, and the pullback digital counter operates to be incremented at one or more of the following transitions: at a transition from 0V to 3V, at a transition from 2V to 5V, and/or at a transition from 0V to 5V; and/or
(vi) using the data acquisition processor having an analog-to-digital converter (ADC), a demodulator, a rotation digital counter, and a pullback digital counter included in the data acquisition processor.

17. The method of claim 12,
wherein the method further comprises one or more of the following:
(i) triggering, via a trigger signal, a single acquisition of a depth scan and recording a value of a rotation digital counter and a pullback digital counter derived from a demodulated encoded synchronization signal that is demodulated with a demodulator of the system and/or of the data acquisition processor of the system;
(ii) triggering, via a trigger signal, a single acquisition of a depth scan on an analog-to-digital converter (ADC) and recording a rotation digital counter and a pullback digital counter derived from a demodulated encoded synchronization signal that is demodulated with a demodulator of the system and/or of the data acquisition processor of the system;
(iii) triggering, via a trigger signal being used as an A-line trigger signal, a sampling of the imaging data, or triggering, via the trigger signal being a k-clock trigger signal, a sampling of the imaging data so as to uniformly acquiring the imaging data in k space;
(iv) using the synchronization signal including or comprising resultant pulse trains which are pulse trains coming from the synchronization processor, wherein the synchronization processor operates to send a pulse corresponding to an index of the first encoder signal which occurs per rotation of the rotary motor except the synchronization processor operates to modify the pulse at a predetermined or set portion of the pullback, the predetermined or set portion of the pullback being one or more of the following: a start of the pullback where the synchronization processor operates to modify the pulses in such a way that the synchronization processor operates to blank or skip one pulse at the start of the pullback, an end of the pullback where the synchronization processor operates to modify the pulses in such a way that the synchronization processor operates to blank or skip one pulse at an end of the pullback, a start and an end of the pullback where the synchronization processor operates to modify the pulses in such a way that the synchronization processor operates to blank or skip one pulse at the start of the pullback and then another pulse at the end of the pullback, a start and/or an end of the pullback where the synchronization processor operates to modify the pulse in such a way that the synchronization processor introduces extra pulses and/or delays at the start of the pullback and/or at the end of the pullback, at an end of the pullback where the synchronization processor operates to modify the pulse to increment a frame counter of the data acquisition processor at a slower rate as the rotary motor is decelerating, and/or at a start of the pullback where the synchronization processor operates to modify the pulse to increment a frame counter of the data acquisition processor towards a steady rate as the rotary motor accelerates to a steady state target; and/or (v) the data acquisition processor includes a frame counter that is incremented once every set number of triggers.

18. The method of claim 17, wherein one or more of the following occurs or exists:
   (i) the data acquisition processor includes a frame counter that is incremented at a fixed, stable, or predetermined or set rate, except at a start of a pullback where the frame counter increments at about half of the predetermined or set rate or at a portion of the predetermined or set rate such that a jump between the start of the pullback and a time when the frame counter is incremented at the fixed, stable, or predetermined or set rate signals or indicates the start and/or the end of the pullback accurately and deduces an approximate or accurate recording of an exact beam position for each depth scan in a case where total pullback length and/or time is known or set;
   (ii) the one or more processors include a control processor that operates to control, or send commands to, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns, and the data acquisition processor includes a frame counter that is incremented at a fixed, stable, or predetermined or set rate, except, in a case where at an end of the pullback where the synchronization processor operates to modify the pulse to increment at a slower rate as the rotary motor is decelerating, the first encoder signal pulse trains are delayed further and the frame counter is incremented at an ever increasing number of A-line triggers, the rotary motor deceleration being controlled by the control processor or the one or more processors to coincide with the end of the pullback accurately to reduce or remove uncertainty between the end of the pullback and the start of the rotary motor deceleration and to determine the end of the pullback accurately and deduce the approximate or accurate recording of the exact beam position for each depth scan for a predetermined or set total pullback length and/or time;
   (iii) the rotary motor has a sharp deceleration profile and the rotary motor operates to decelerate significantly or substantially in one rotation for the number of A-line triggers occurring before a frame counter of the data acquisition processor is incremented such that the deceleration profile of the rotary motor is large enough to be detected as the rotary motor slowing down rather than be detected as a variation in rotary motor rotation speed; and/or
   (iv) a variation in rotary motor speed operates to lead in normal operation to a pulse train every predetermined or set number of A-line triggers and a rotary motor deceleration during the time equivalent of one steady state rotation operates to be another number of A-line triggers that is larger than the predetermined or set number of A-line triggers such that a threshold value operates to be set or selected above the predetermined or set number of A-line triggers and below the another number of A-line triggers to detect the end of the pullback.

19. The method of claim 18, further comprising one or more of the following occurs or exists:
   (i) determining, via a pullback status processor of the one or more processors, a pullback status indicating or detecting the start and/or the end of the pullback;
   (ii) initiating a deceleration of the rotary motor by the rotary motor controller and/or by the rotary motor controller and a driver, wherein the rotary motor controller and/or the driver operate to receive a command to control deceleration from the pullback status processor;
   (iii)) receiving, via the pullback status processor, information from the rotary motor controller and/or a driver to determine the pullback status; and/or
   (iv) using the pullback status processor while the pullback status processor is disposed or is included in the scanning mechanism of the system.

20. The method of claim 17, wherein one or more of the following occurs or exists:
   (i) the rotary motor is rotated at a velocity that is lower than a target steady state value, and then accelerated at or about the same time as the pullback motor is accelerated;
   (ii) the data acquisition processor includes a frame counter that is incremented at a fixed, stable, or predetermined or set rate once or as the rotary motor accelerates to the target steady state value;
   (iii) the one or more processors include a control processor that operates to control, or send commands to, the rotary motor controller and the pullback motor controller such that set or predetermined velocities and/or positions of the catheter or probe, and/or set or predetermined velocities and/or positions of the rotary motor and/or the pullback motor, are achieved to yield one or more scan patterns, and the rotary motor acceleration is controlled by the control processor or the one or more processors to coincide with the start of the pullback accurately to reduce or remove uncertainty between the start of the pullback and the start of the rotary motor acceleration and to determine the start of the pullback accurately and deduce the approximate or accurate recording of the exact beam position for each depth scan for a predetermined or set total pullback length and/or time;
   (iv) the rotary motor has a sharp acceleration profile and the rotary motor operates to accelerate significantly or substantially in one rotation for the number of A-line triggers occurring before a frame counter of the data acquisition processor is incremented such that the acceleration profile of the rotary motor is large enough to be detected as the rotary motor speeding up to the target steady state value rather than be detected as a variation in rotary motor rotation speed; and/or (v) a variation in rotary motor speed pre-pullback operates to lead to a pulse train every predetermined or set number of A-line triggers and the rotary motor acceleration during the time equivalent of one steady state rotation operates to be another number of A-line triggers that is larger than the predetermined or set number of A-line triggers such that a threshold value operates to be set or selected above the predetermined or set number of A-line triggers and below the another number of A-line triggers to detect the start of the pullback.

21. The method of claim 20, further comprising one or more of the following:

(i) determining, via a pullback status processor of the one or more processors, a pullback status indicating or detecting the start and/or the end of the pullback;

(ii) initiating the acceleration of the rotary motor by the rotary motor controller and/or by the rotary motor controller and a driver, wherein the rotary motor controller and/or the driver operate to receive a command for controlling the acceleration from the pullback status processor;

(iii) receiving, via the pullback status processor, information from the rotary motor controller and/or a driver to determine the pullback status; and/or (iv) using the pullback status processor while the pullback status processor is disposed or is included in the scanning mechanism of the system.

22. A non-transitory computer-readable storage medium storing at least one program that operates to cause one or more processors to execute a method for performing image synchronization for one or more imaging modalities of a system, the method comprising:

using one or more imaging modalities to obtain imaging data using an imaging apparatus of the system;

performing beam scanning, via a scanning mechanism of the system using a rotary motor of the system and a pullback motor of the system, of a catheter or probe of the system to obtain a beam position of the catheter or probe, the rotary motor operating to rotate the scanning mechanism, a part of the scanning mechanism, and/or the catheter or probe, and the pullback motor operating to control pullback of the catheter or probe;

achieving image synchronization, via one or more processors of the system, by recording the beam position simultaneously or contemporaneously with the imaging data and enabling accurate spatial registration of the imaging data;

controlling, or sending commands to, via the one or more processors of the system, a rotary motor controller of the system and a pullback motor controller of the system; and conditioning or controlling, via a synchronization processor of the one or more processors, first and second encoder signals before the synchronization processor interfaces with a data acquisition processor of the one or more processors such that each time a depth scan is acquired on the imaging data input, information from the first and second encoder signals is recorded for each of the rotary motor and the pullback motor to record an exact or approximate beam position for the depth scan, and the synchronization processor operates to use a single synchronization signal for the data acquisition processor to capture a position of the catheter or probe for each measured depth scan profile, wherein the system further includes the first encoder signal that operates to be available to the rotary motor controller and the second encoder signal that operates to be available to the pullback motor controller.

* * * * *